(12) United States Patent
Buri et al.

(10) Patent No.: US 11,911,601 B2
(45) Date of Patent: Feb. 27, 2024

(54) CANNULA INSERTION MECHANISM

(71) Applicant: TecMed AG, Burgdorf (CH)

(72) Inventors: Thomas Buri, Burgdorf (CH); Christophe Hofer, Burgdorf (CH); Patrick Hostettler, Hasle (CH); Seline Staub, Winterthur (CH); Jürg Steck, Kirchberg (CH); Ursina Streit, Schönbühl (CH)

(73) Assignee: TecMed AG, Burgdorf (CH)

( * ) Notice: Subject to any disclaimer, the term of this patent is extended or adjusted under 35 U.S.C. 154(b) by 846 days.

(21) Appl. No.: 16/904,815

(22) Filed: Jun. 18, 2020

(65) Prior Publication Data
US 2020/0316314 A1    Oct. 8, 2020

Related U.S. Application Data

(63) Continuation of application No. PCT/IB2018/059688, filed on Dec. 6, 2018.

(30) Foreign Application Priority Data

Dec. 21, 2017 (EP) .................. 17209764

(51) Int. Cl.
*A61M 5/32*     (2006.01)
*A61M 5/158*    (2006.01)

(52) U.S. Cl.
CPC ... *A61M 5/3287* (2013.01); *A61M 2005/1585* (2013.01); *A61M 2205/36* (2013.01)

(58) Field of Classification Search
CPC ........... A61M 2005/14252; A61M 2005/1585; A61M 5/3287; A61M 2205/36
See application file for complete search history.

(56) References Cited

U.S. PATENT DOCUMENTS 7,128,727 B2    10/2006  Flaherty et al.
7,909,791 B2     3/2011  Liniger et al.
(Continued)

FOREIGN PATENT DOCUMENTS

CH    713377 A2    7/2018
CH    713378 A2    7/2018
(Continued)

OTHER PUBLICATIONS

"International Preliminary Report on Patentability", Application No. PCT/IB2018/050166, dated Jul. 23, 2019, 7 pages.
(Continued)

*Primary Examiner* — Tiffany Legette
(74) *Attorney, Agent, or Firm* — Dorsey & Whitney LLP

(57) ABSTRACT

An insertion mechanism for a cannula includes a cannula housing, a displaceable cannula, at least one cannula holder, an insertion spring, a triggering element, and a safety device. The safety device, in a secured state, holds the triggering element in a blocked position against a force of the insertion spring and, in a released state, releases the triggering element such that the triggering element is movable into a release position by the force of said insertion energy store and the at least one cannula holder is able to move relative to the cannula housing, driven by the insertion energy store, so as to trigger or implement an insertion movement or insertion. To reach the released state, the safety mechanism is heatable by a heating element and softened and/or weakened with respect to its mechanical carrying or holding capacity, or severed or at least partially or completely melted.

22 Claims, 33 Drawing Sheets

(56) References Cited

U.S. PATENT DOCUMENTS

| | | |
|---|---|---|
| 9,220,838 B2 | 12/2015 | Soma et al. |
| 2005/0222537 A1 | 10/2005 | Dinsmoor et al. |
| 2014/0142508 A1 | 5/2014 | Diianni et al. |
| 2014/0228759 A1* | 8/2014 | Soma .................... A61M 5/20 604/164.01 |
| 2015/0174317 A1 | 6/2015 | Momose |
| 2017/0165451 A1 | 6/2017 | Frey et al. |

FOREIGN PATENT DOCUMENTS

| | | |
|---|---|---|
| CH | 713379 A2 | 7/2018 |
| CH | 713403 A2 | 7/2018 |
| EP | 2762183 A1 | 8/2014 |
| EP | 3501577 A1 | 6/2019 |
| GB | 2396298 A | 6/2004 |
| WO | 9902208 A1 | 1/1999 |
| WO | 2012143434 A2 | 10/2012 |
| WO | 2013153041 A2 | 10/2013 |
| WO | 2016145094 A2 | 9/2016 |
| WO | 2019123074 A1 | 6/2019 |

OTHER PUBLICATIONS

"International Search Report and Written Opinion", Application No. PCT/IB2018/050166, dated Apr. 9, 2018, 17 pages.
International Preliminary Report on Patentability received for International Application No. PCT/IB2018/059688, dated Jun. 23, 2020, 12 pages.

* cited by examiner

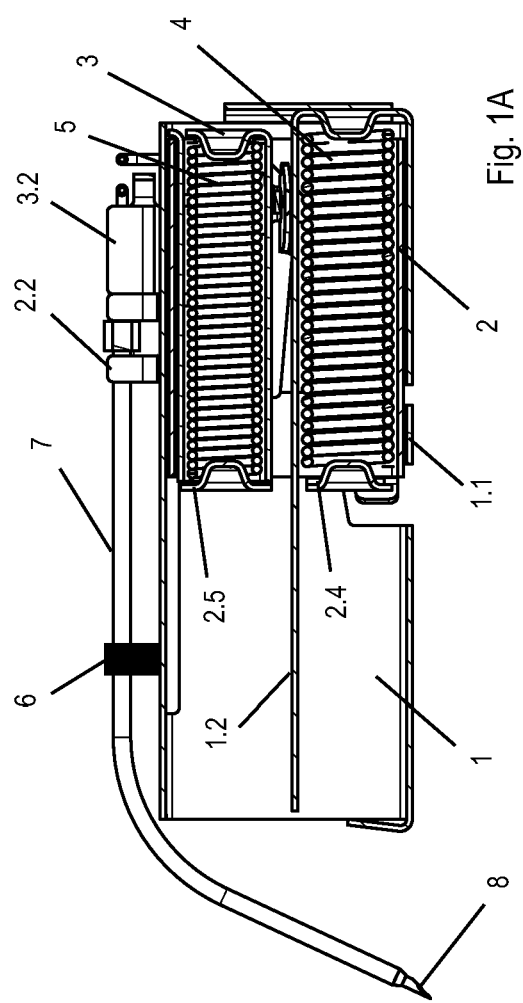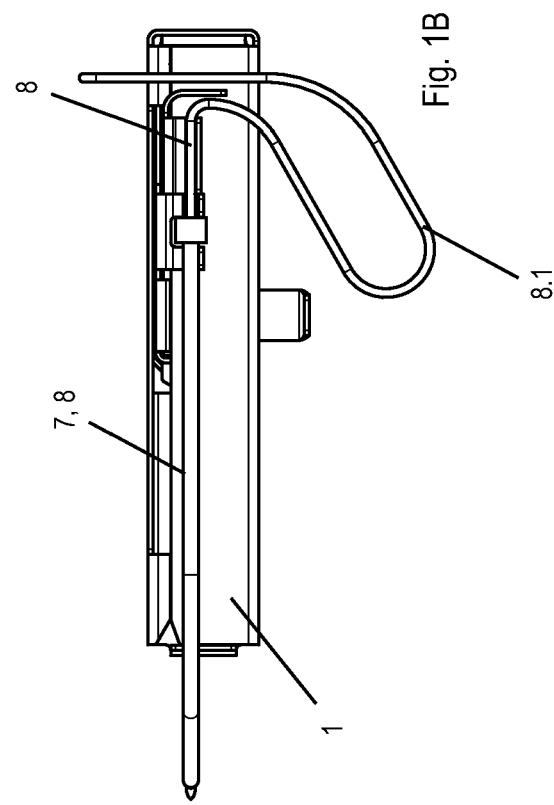

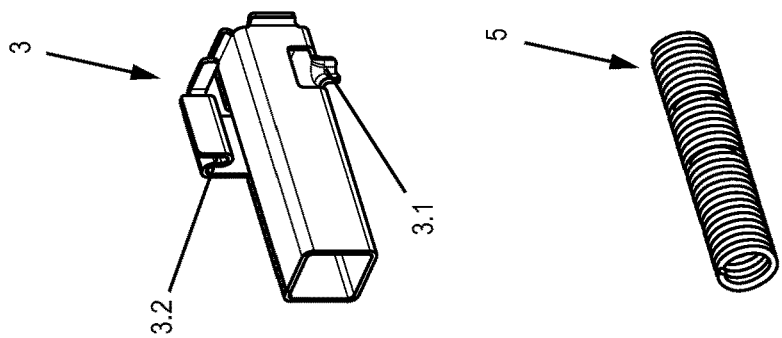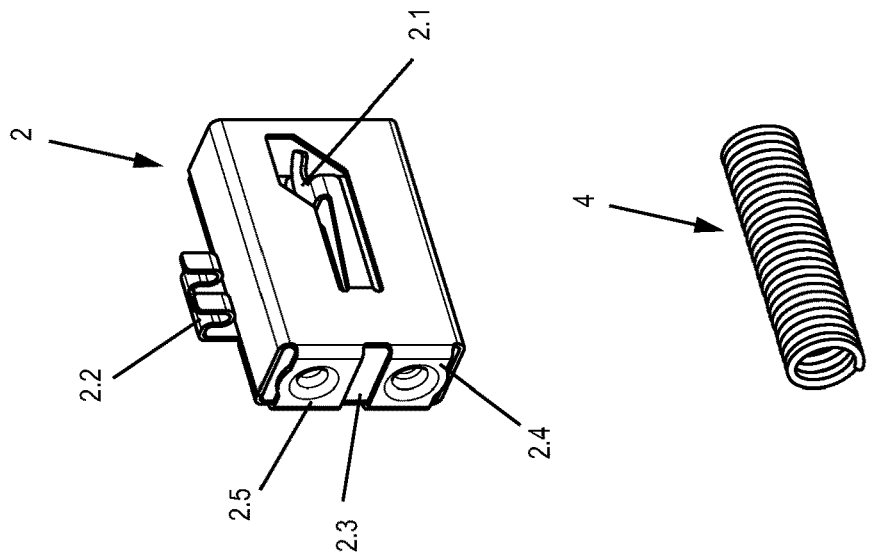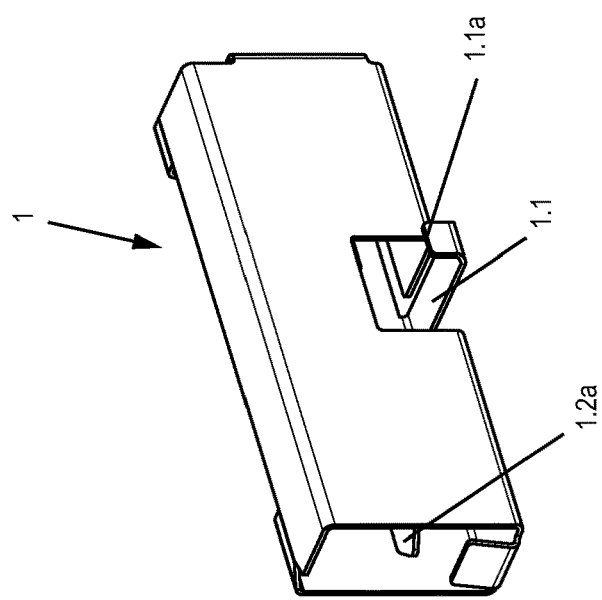
Fig. 4

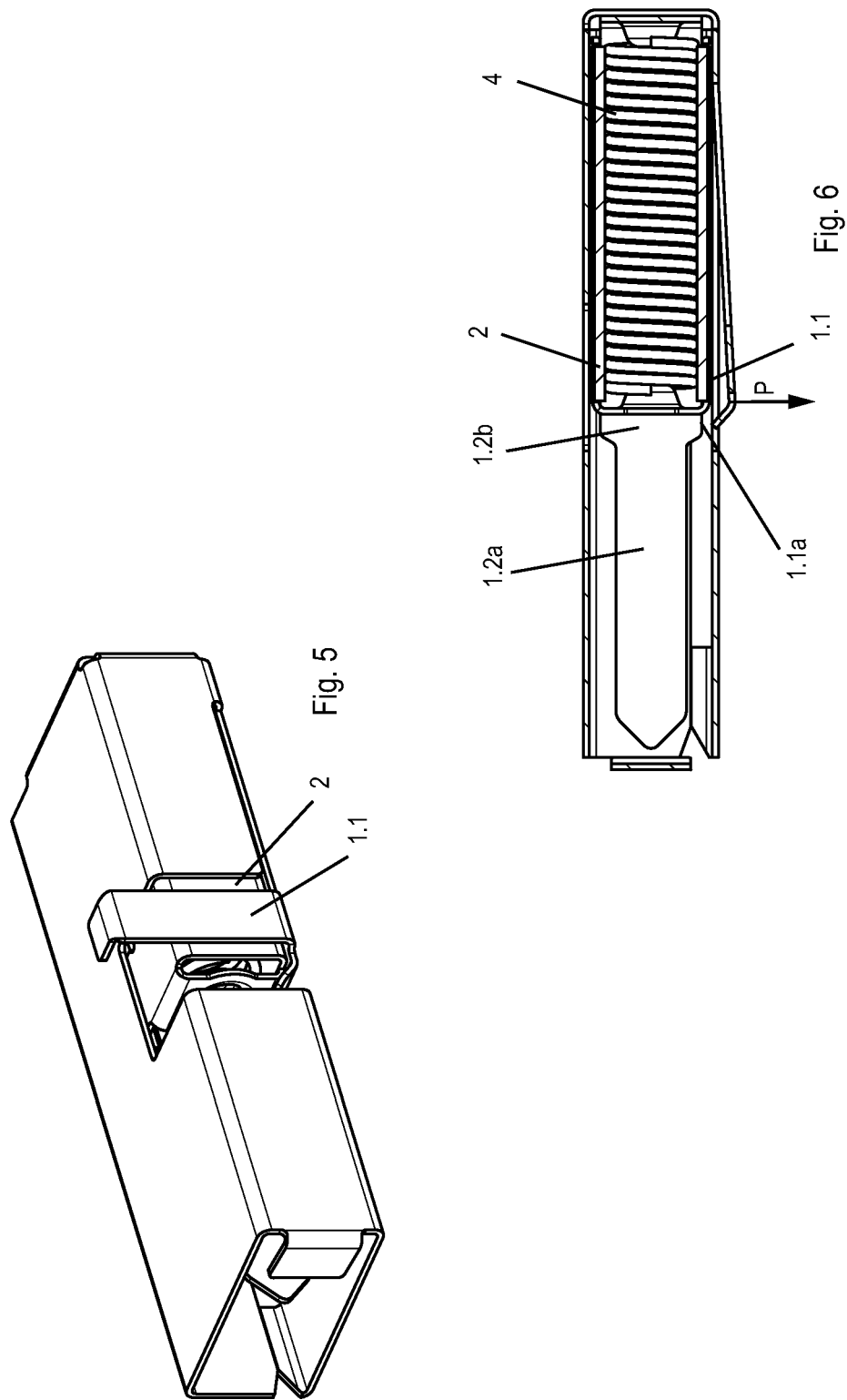

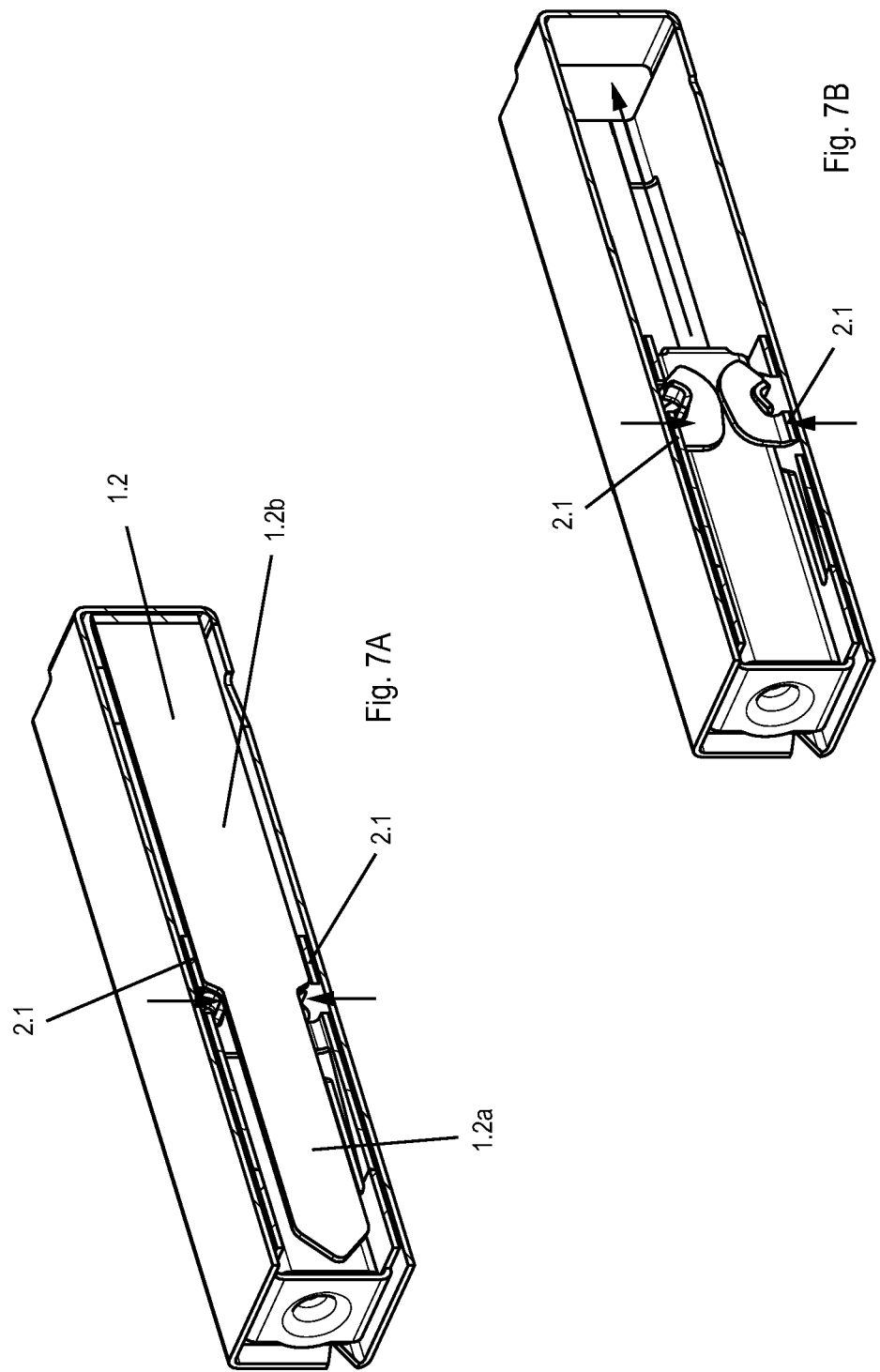

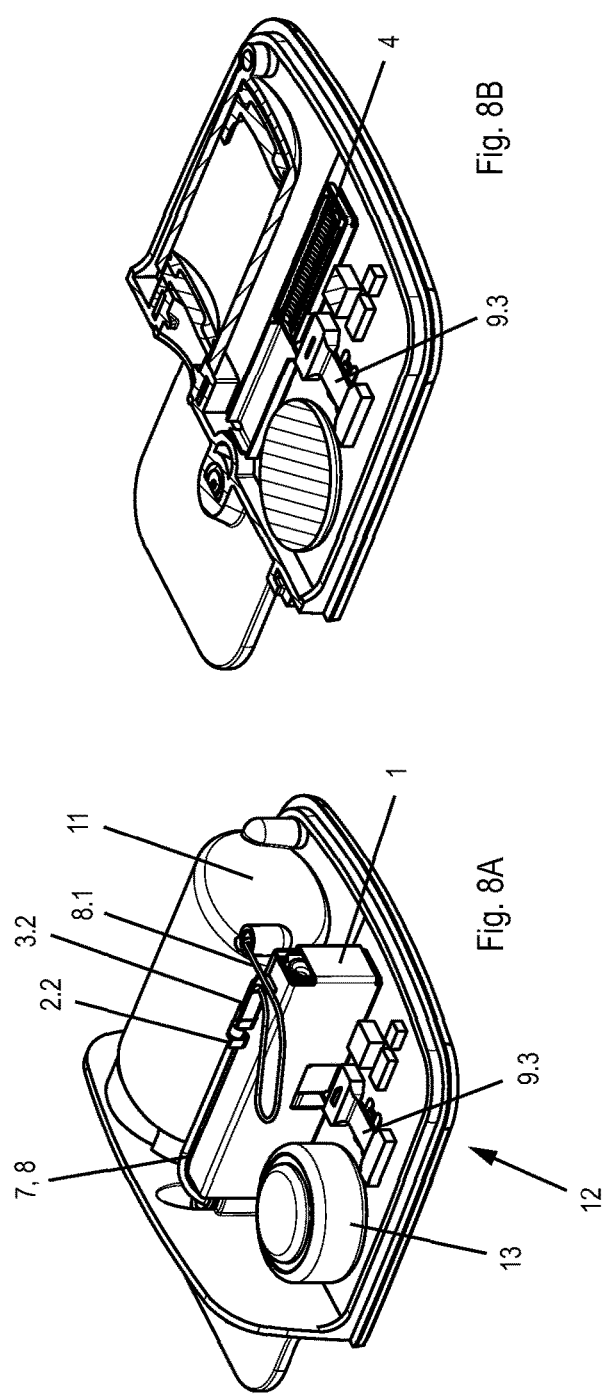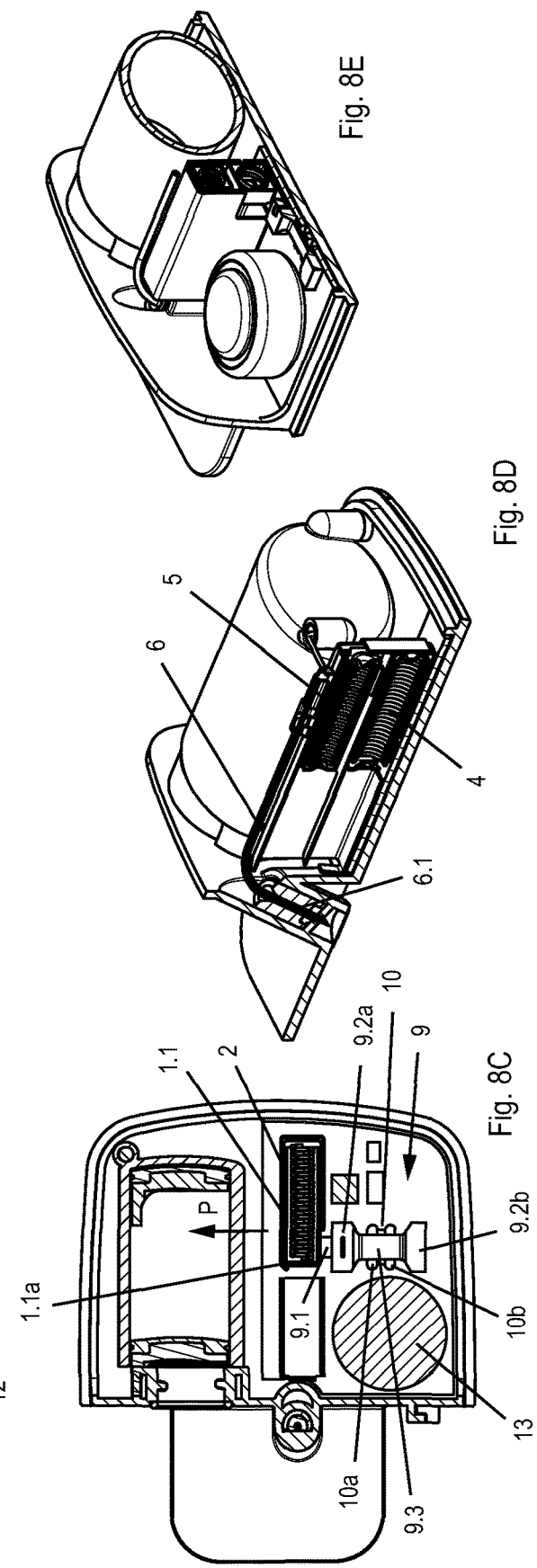

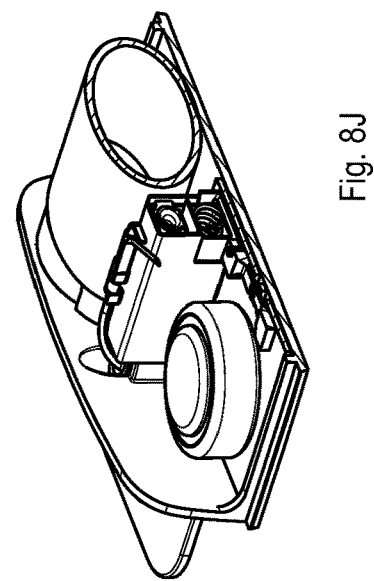
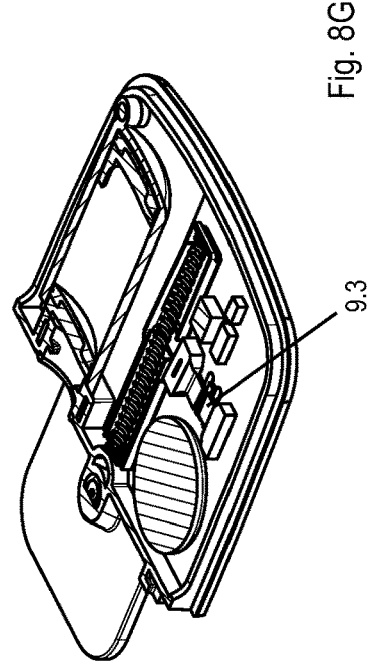
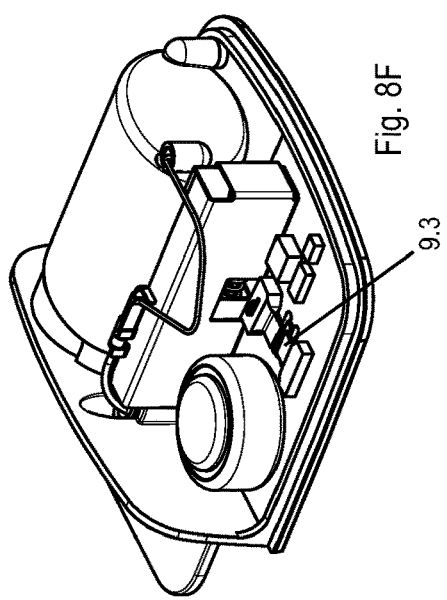
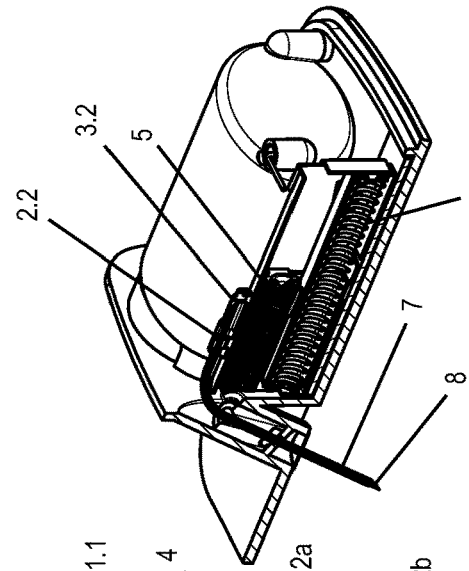
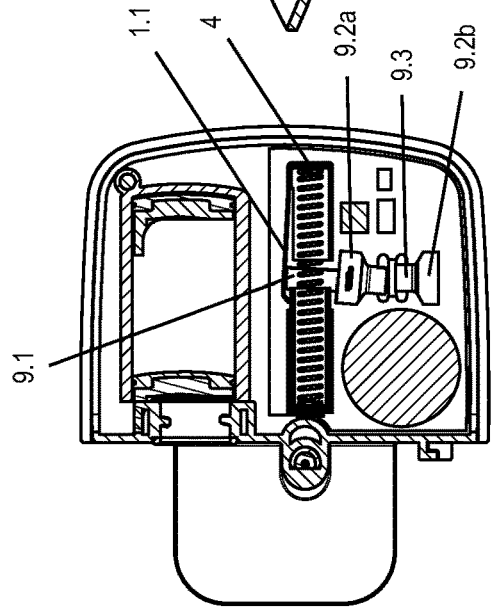

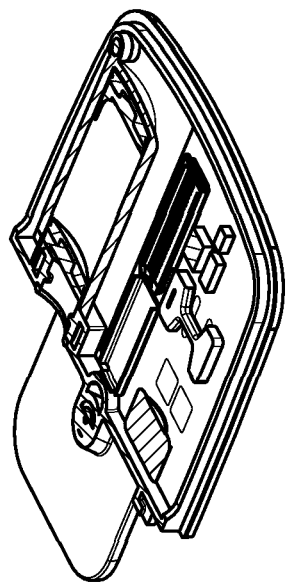
Fig. 9B
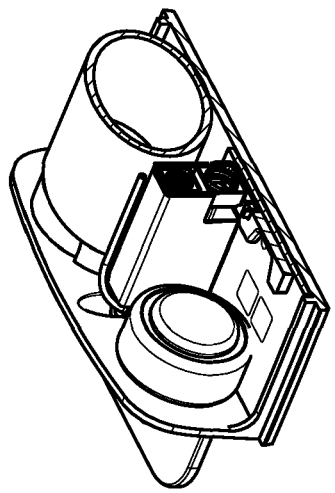
Fig. 9E
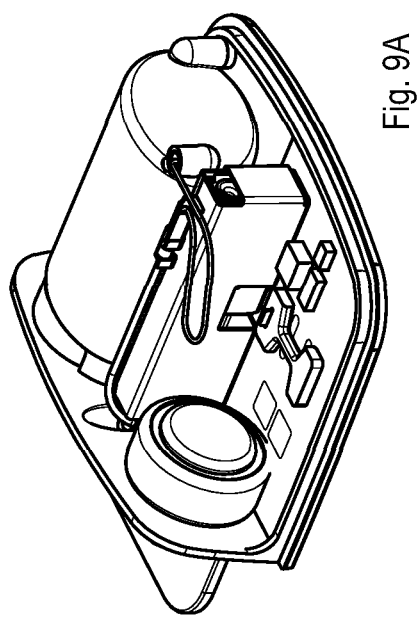
Fig. 9A
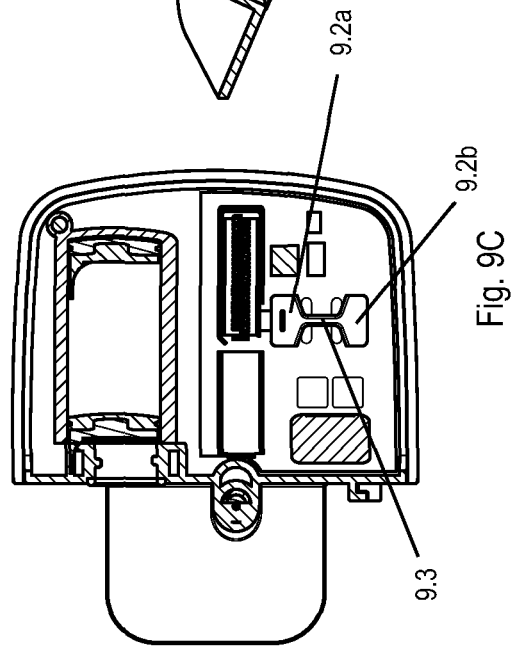
Fig. 9D
Fig. 9C

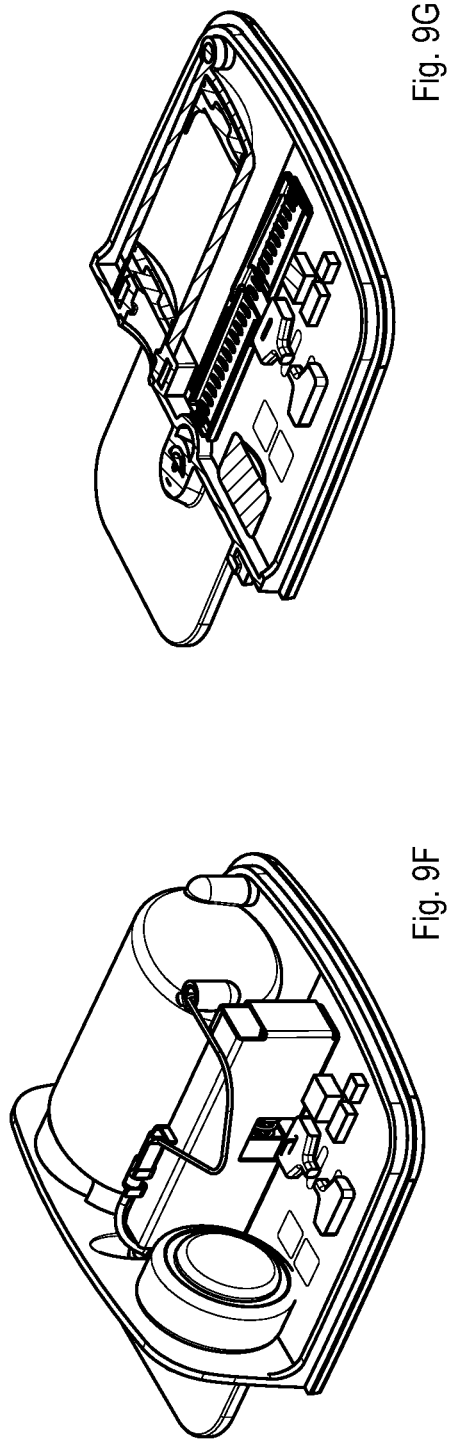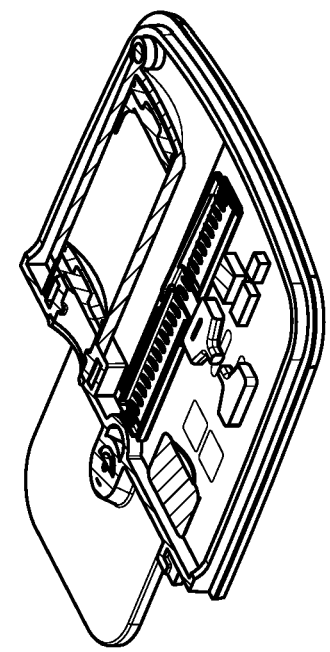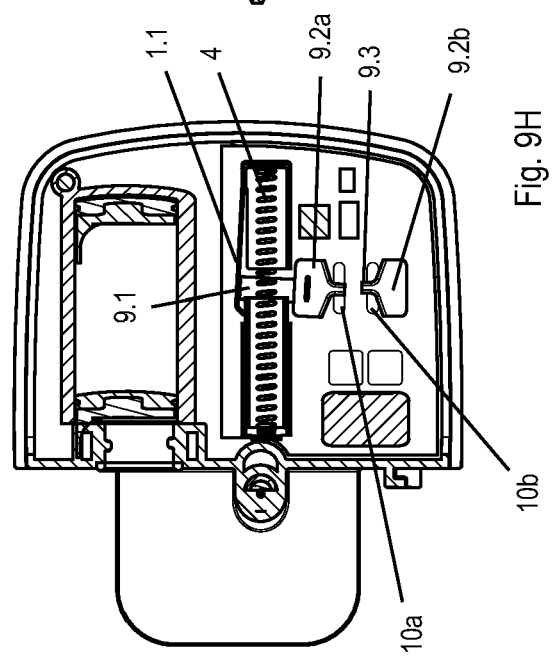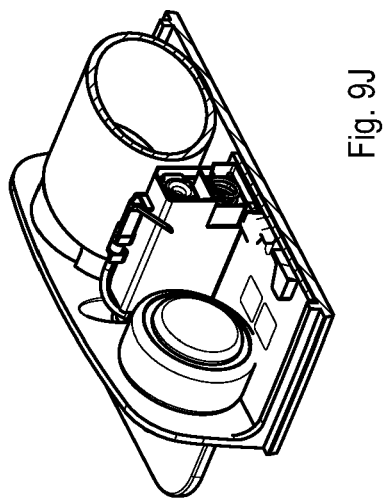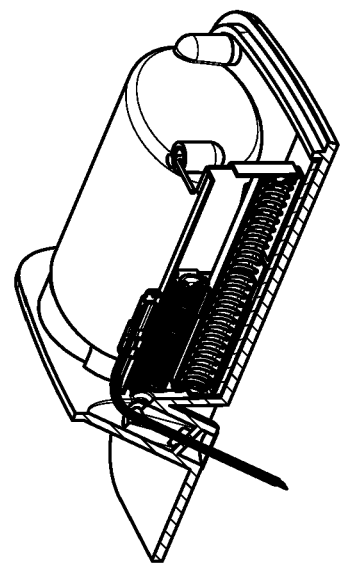

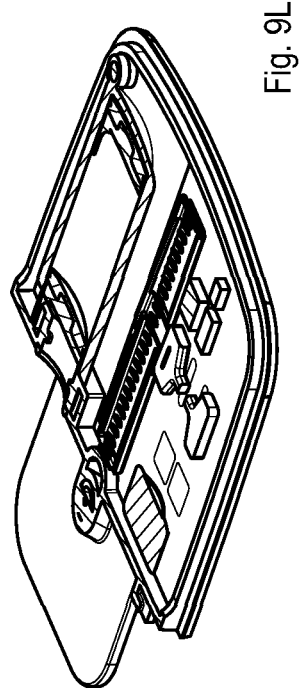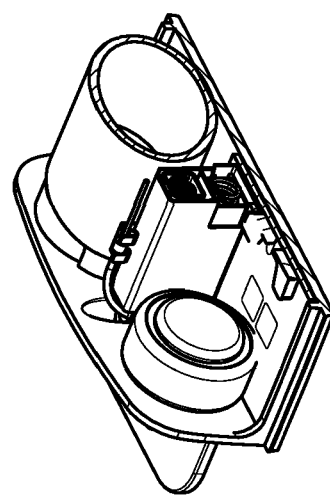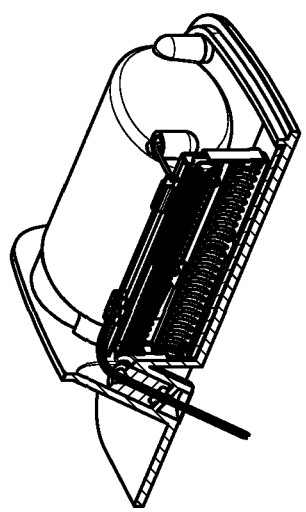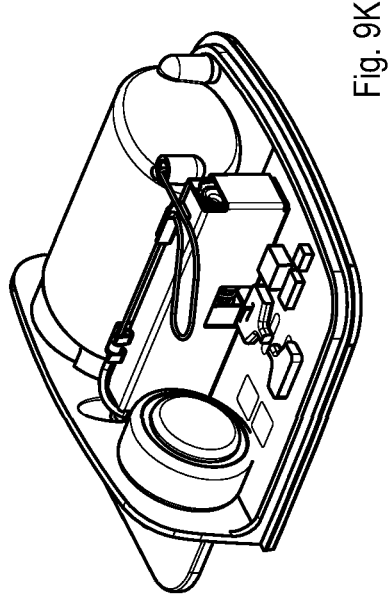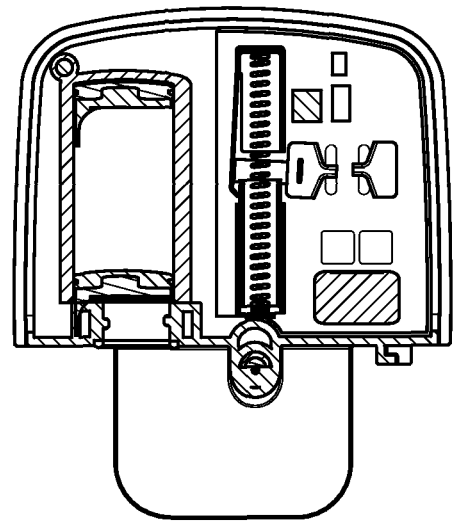

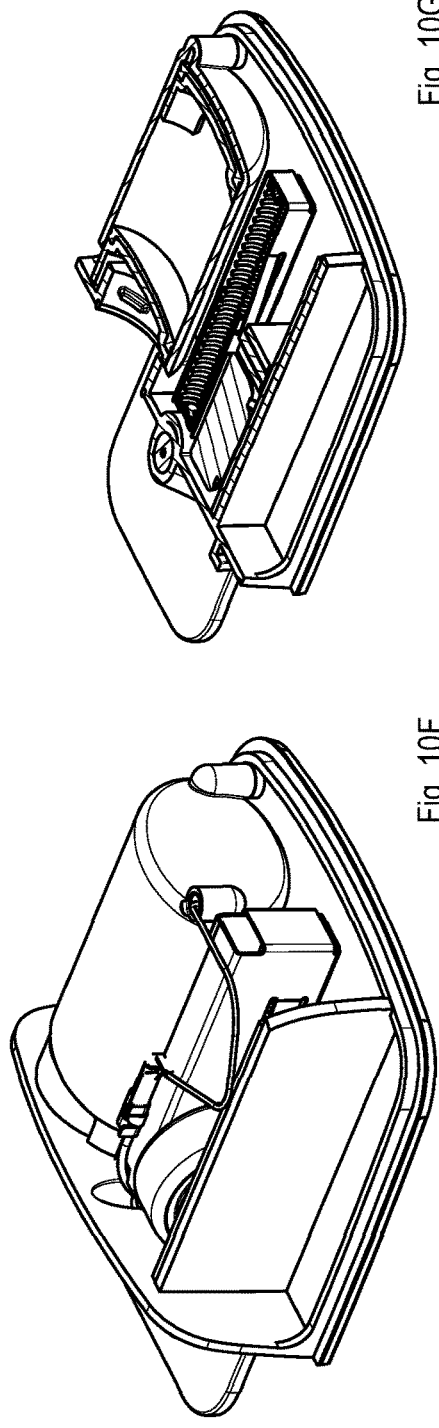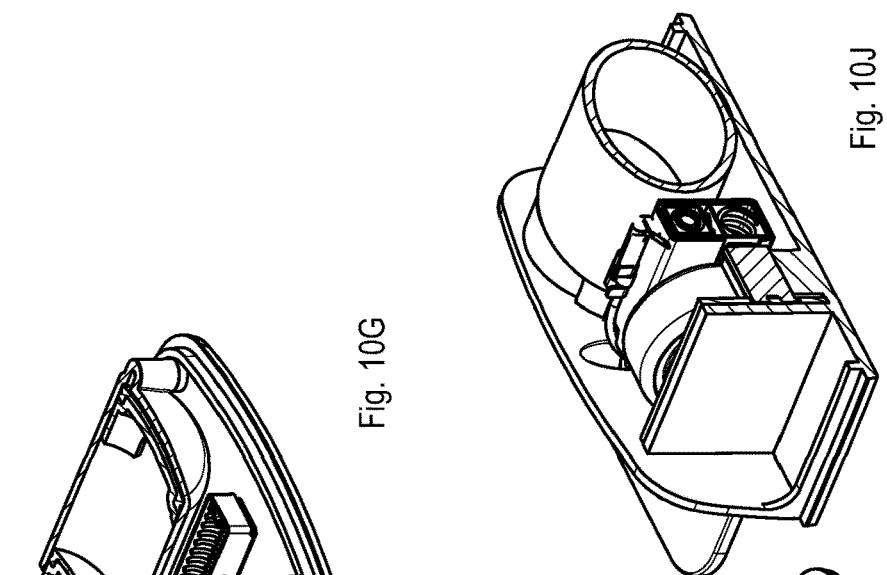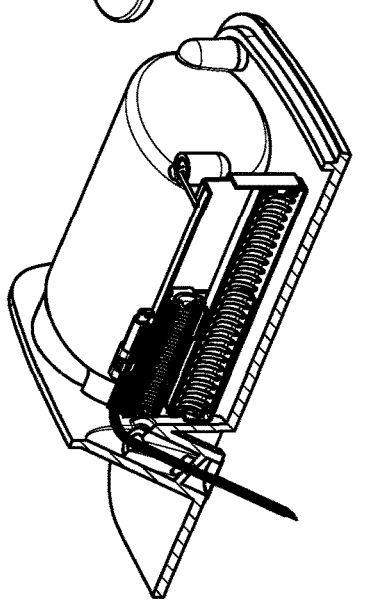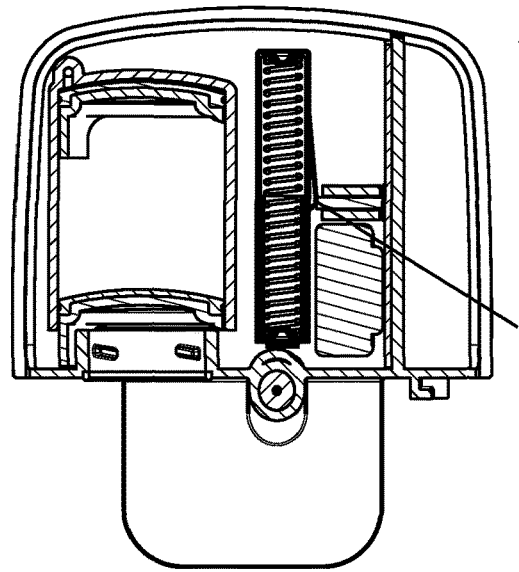

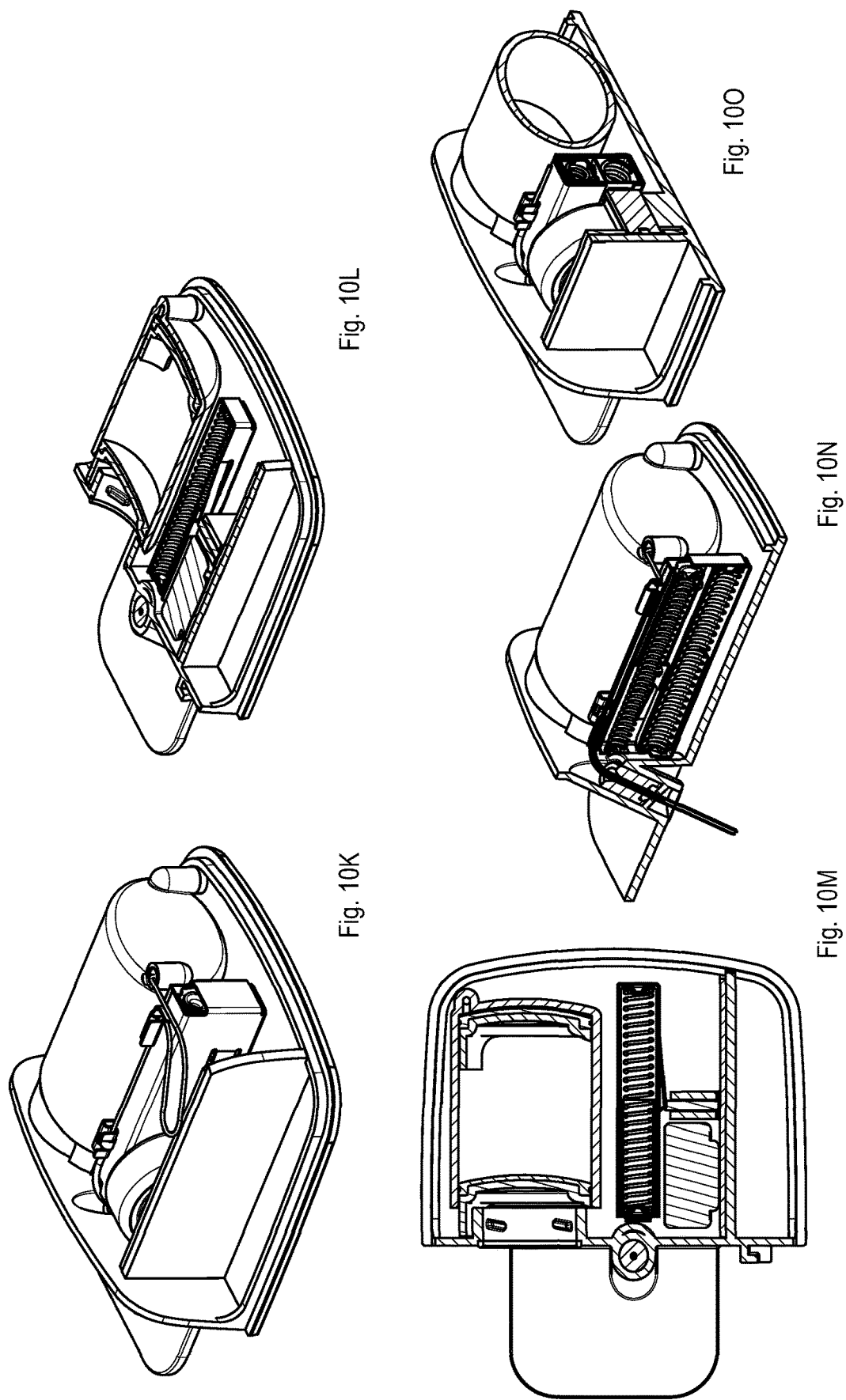

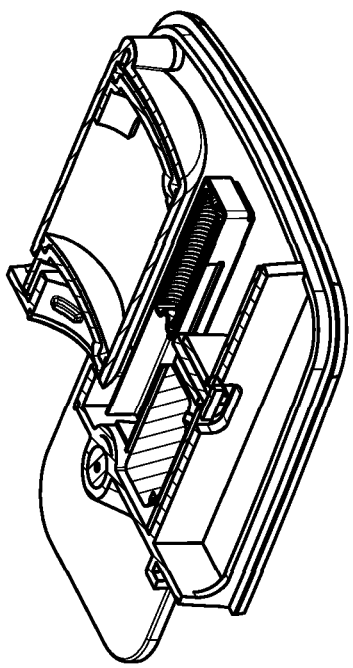
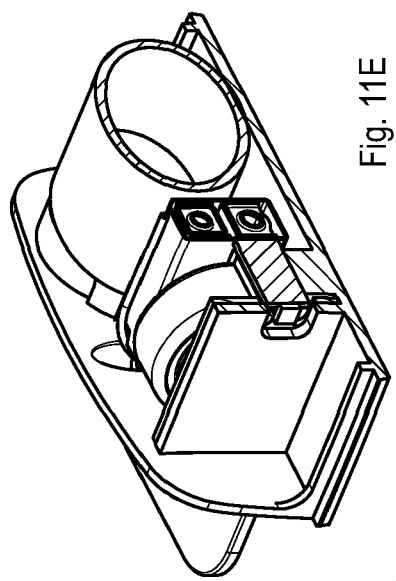
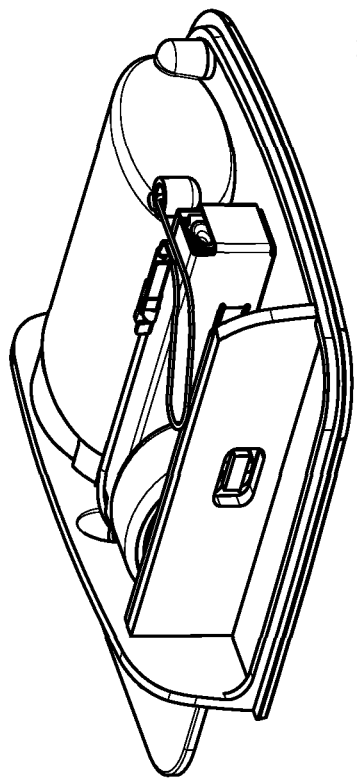
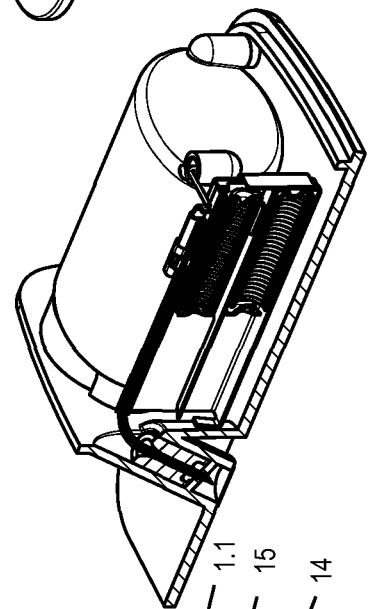
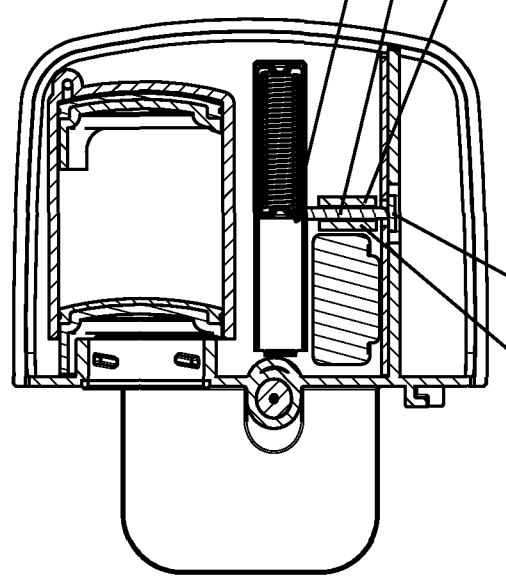

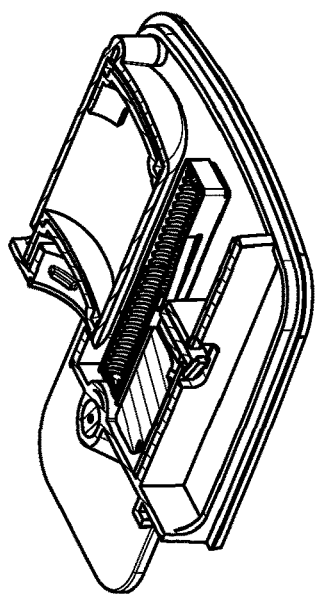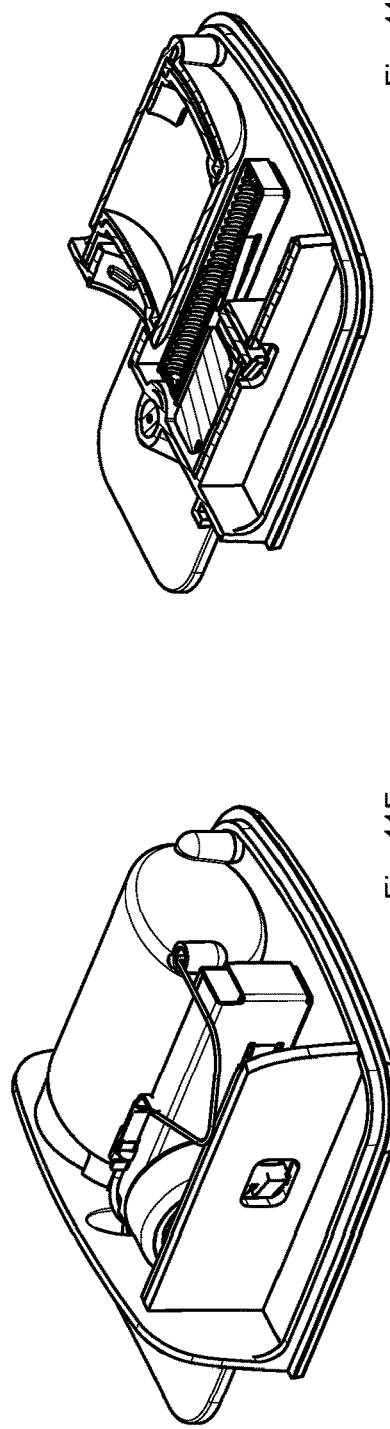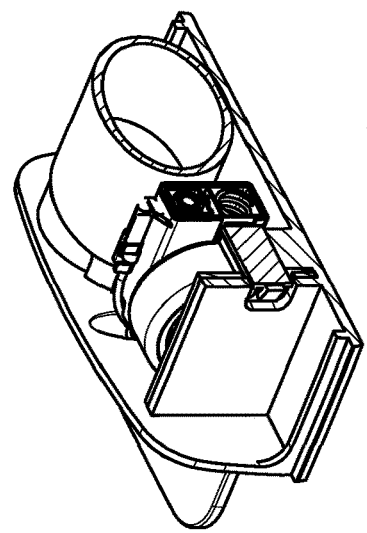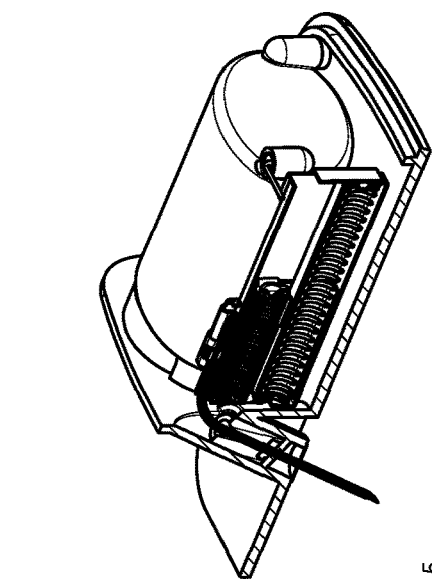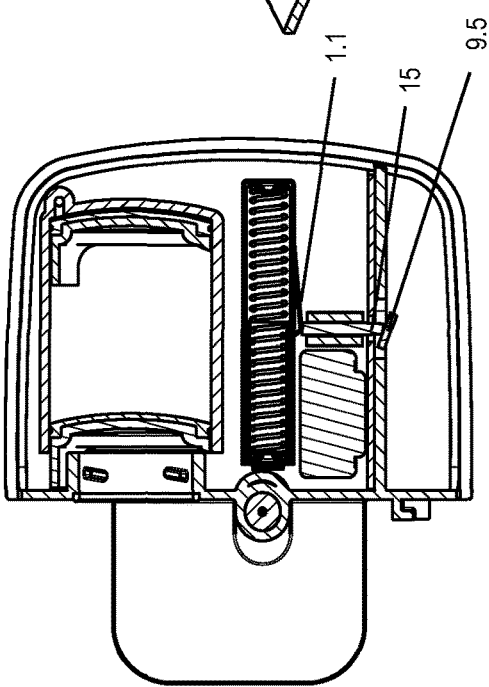

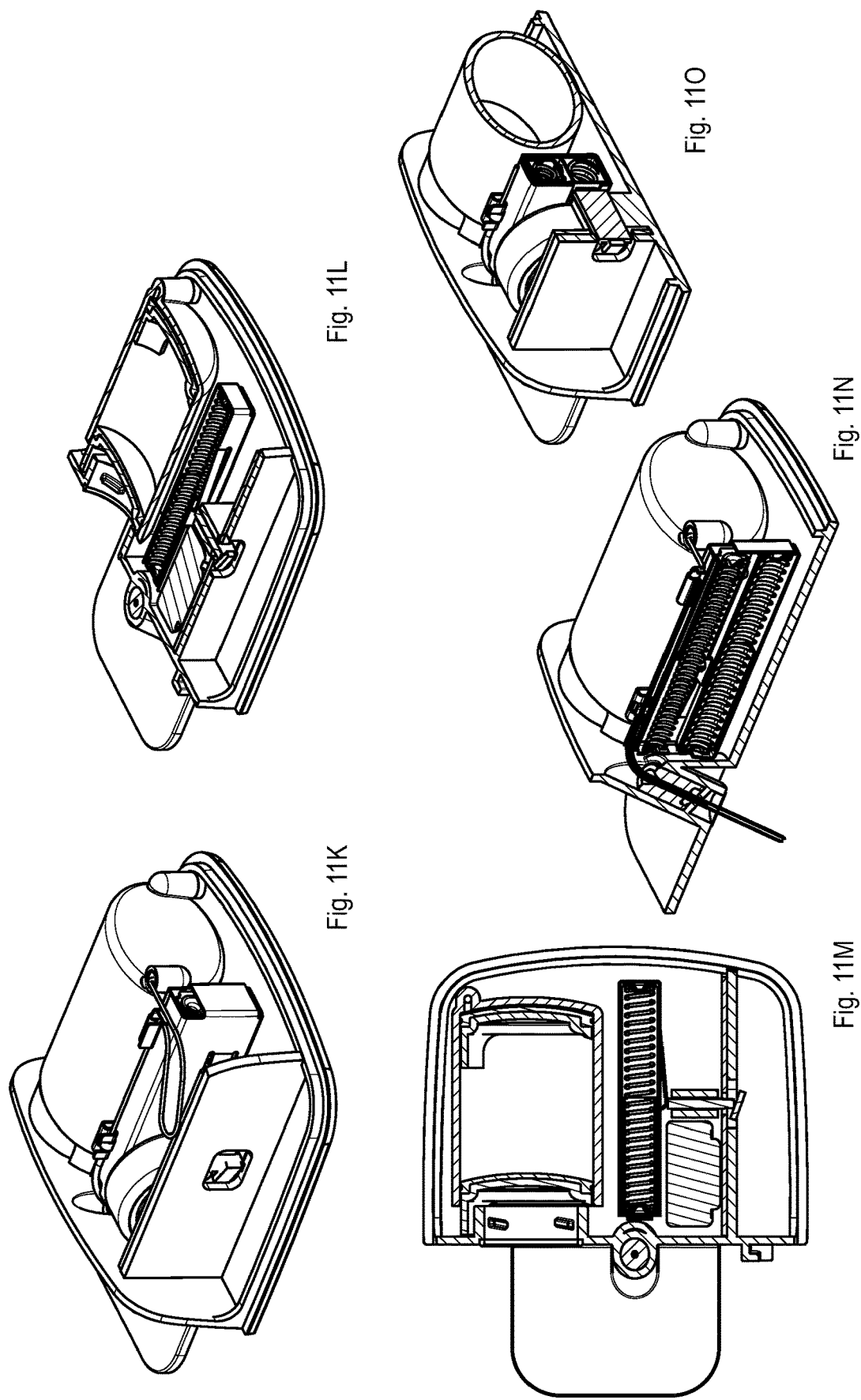

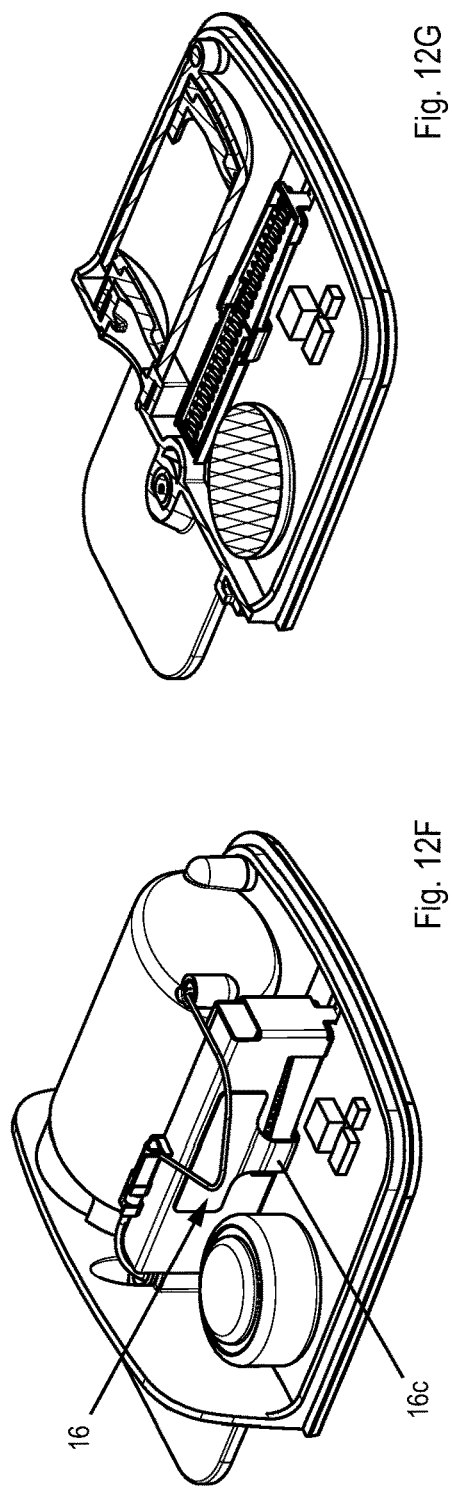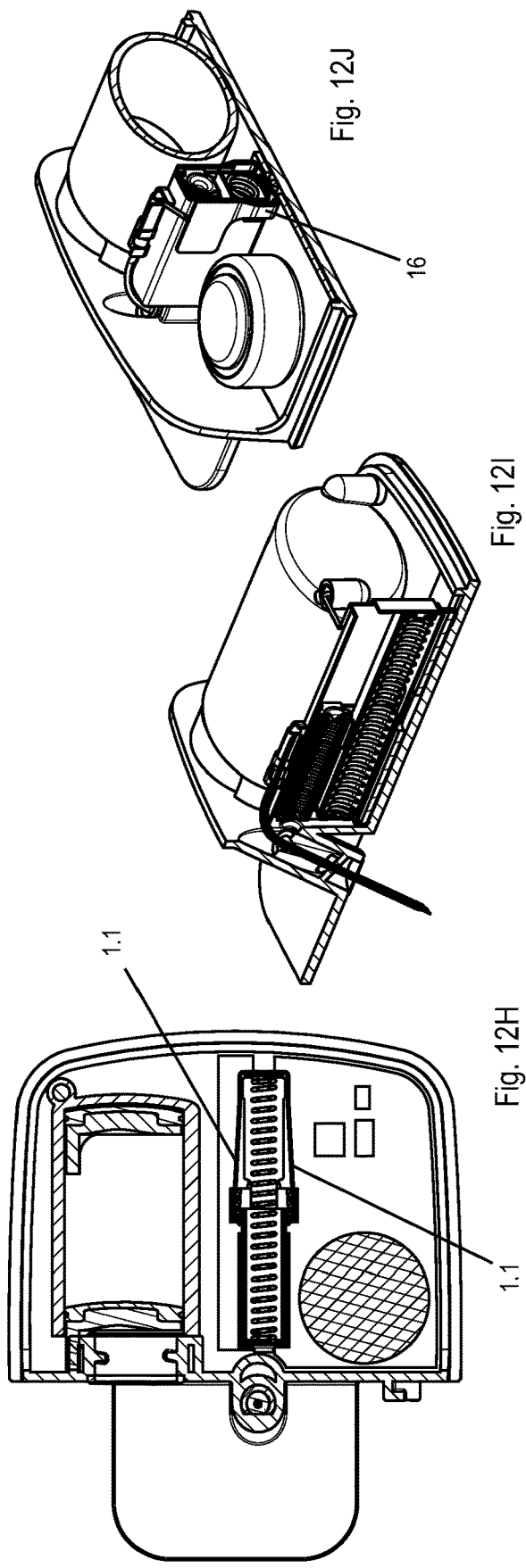

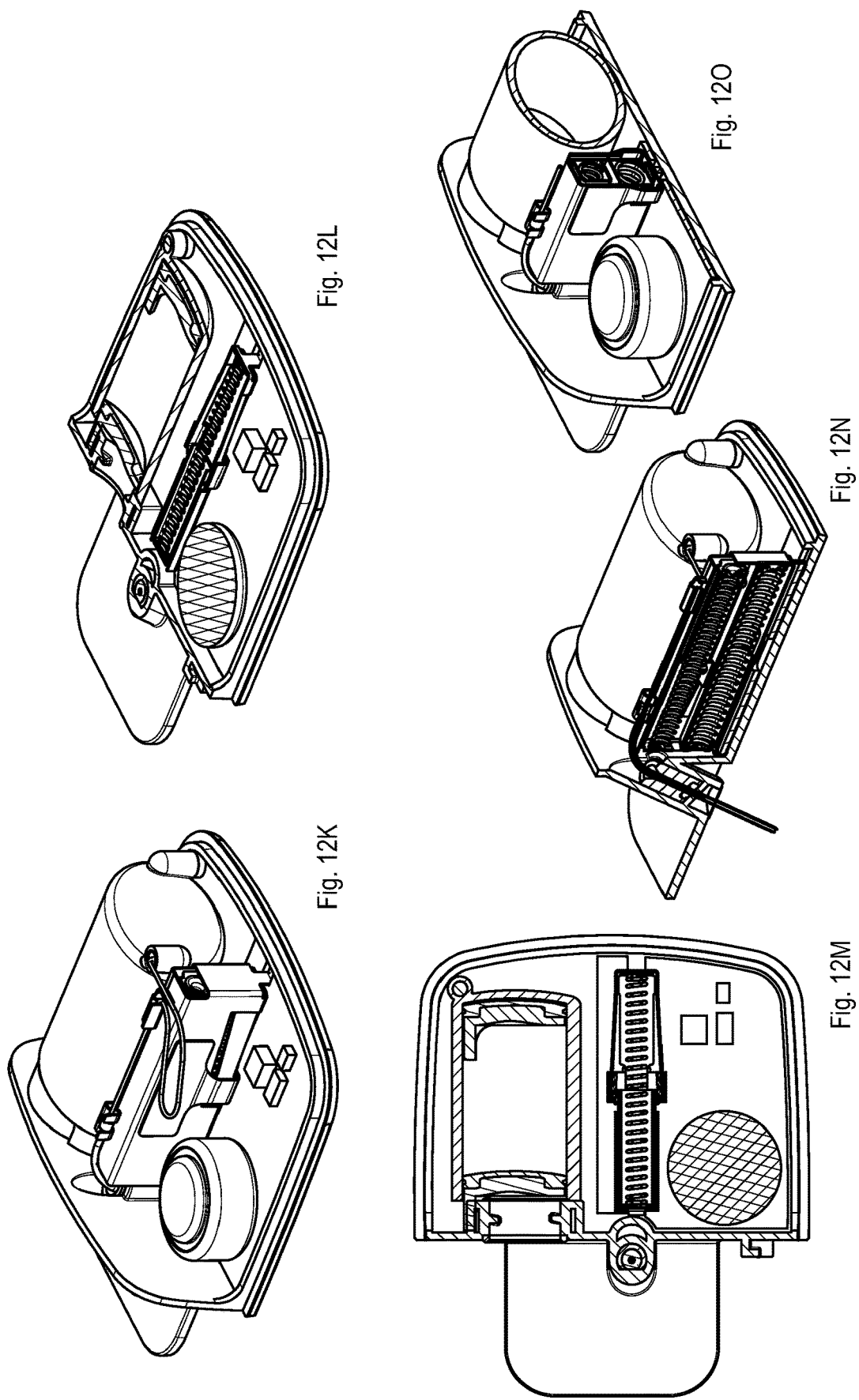

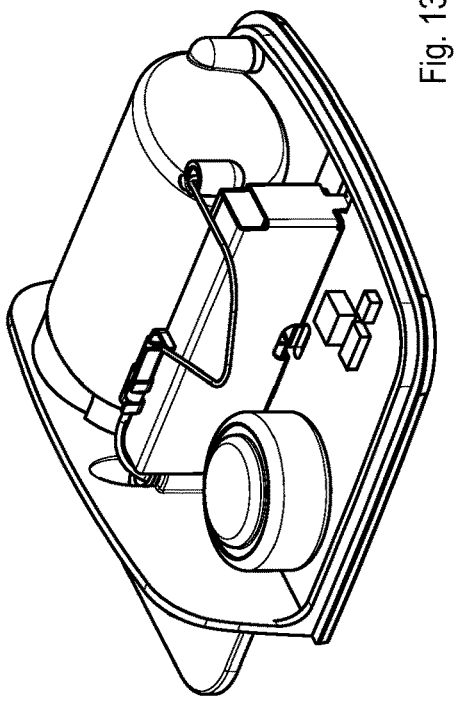
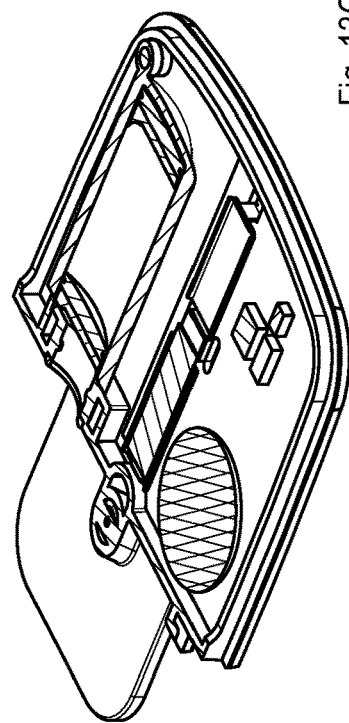
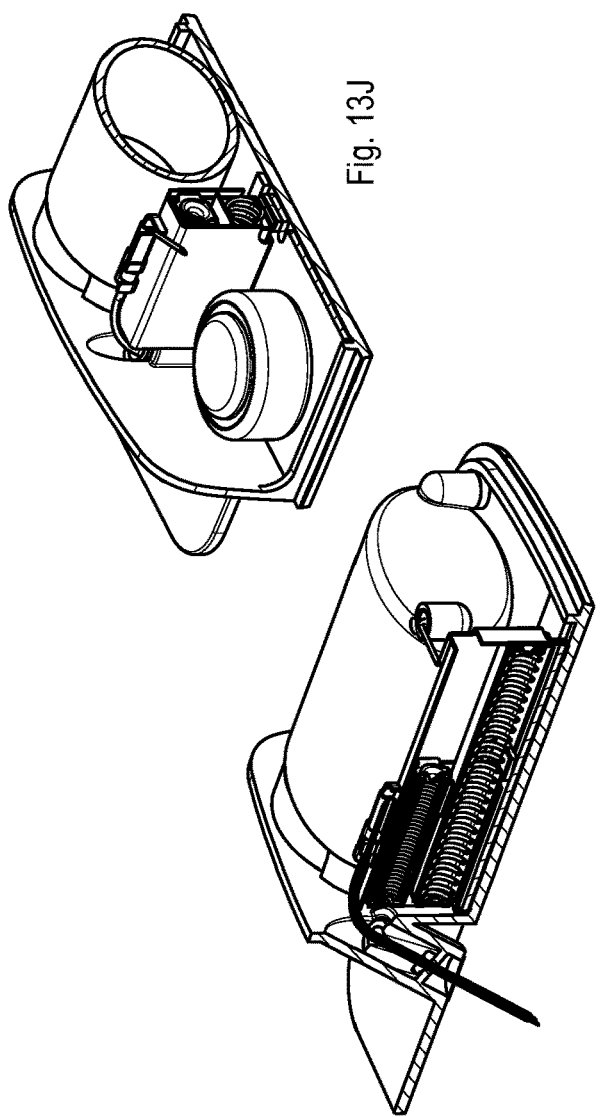
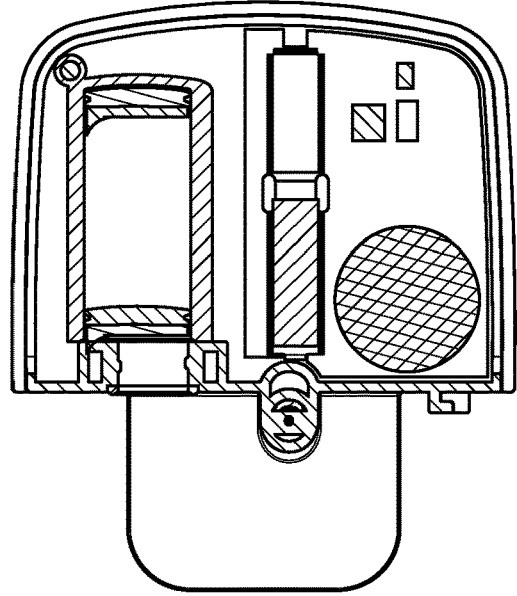

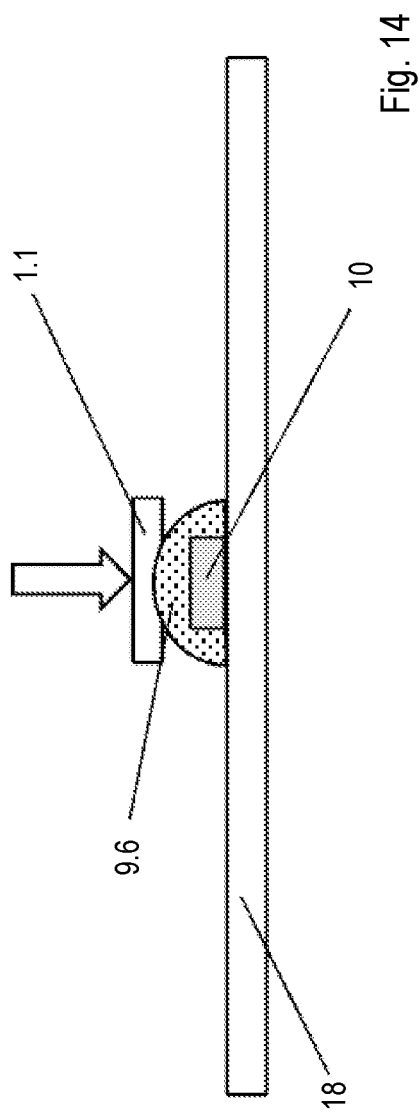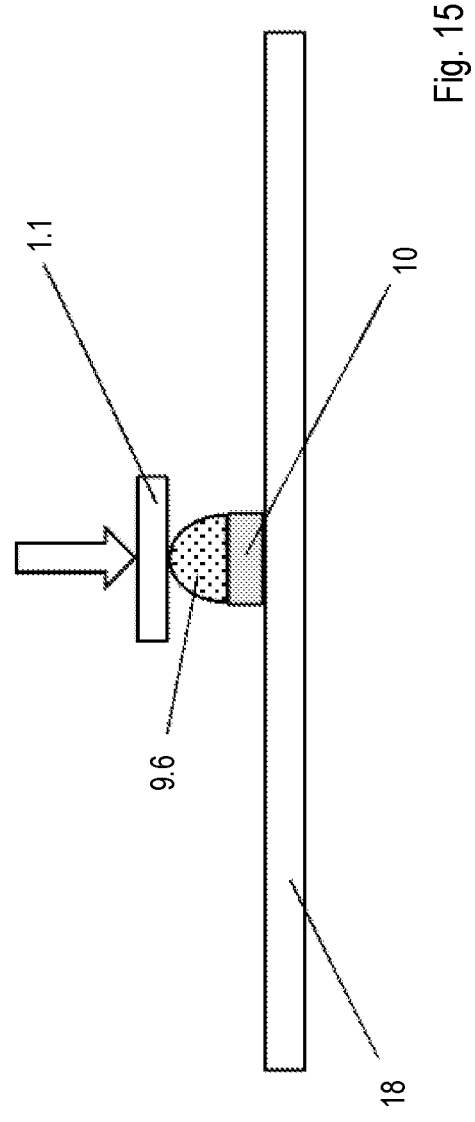

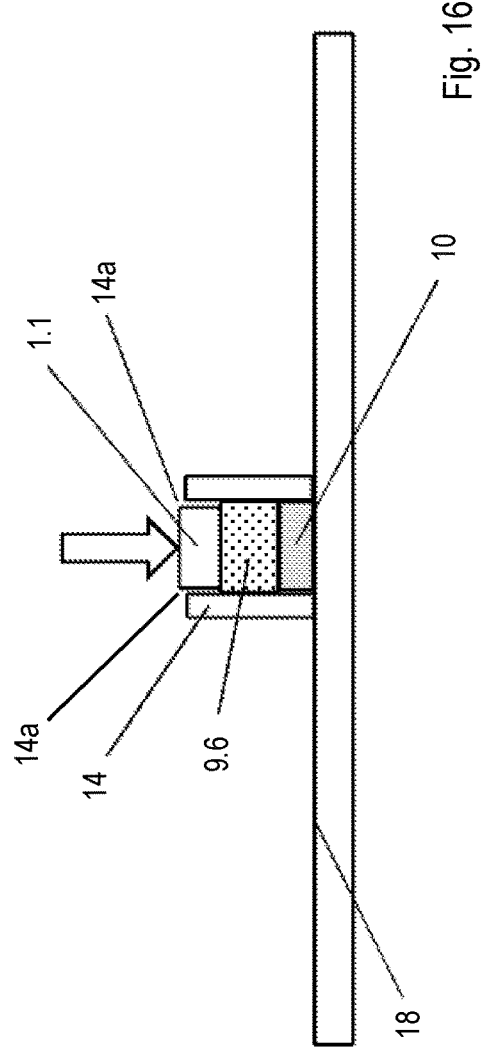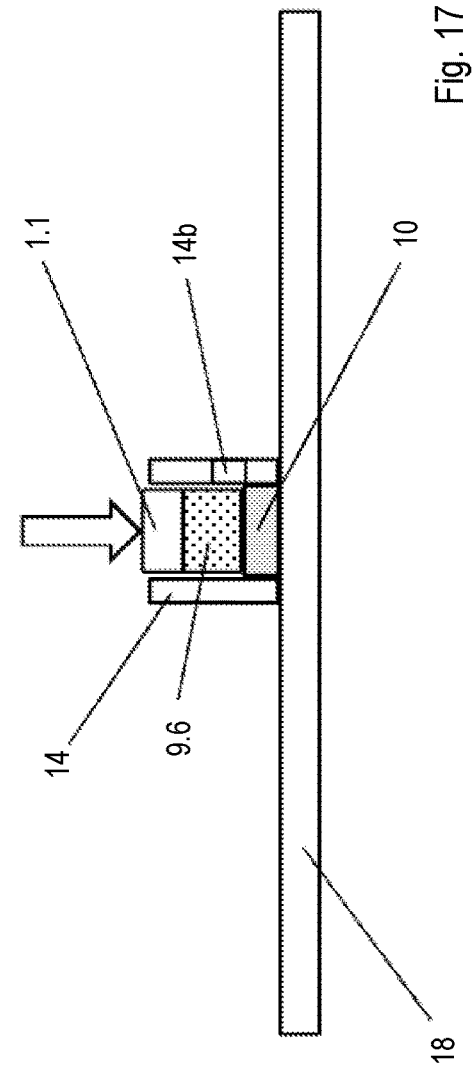

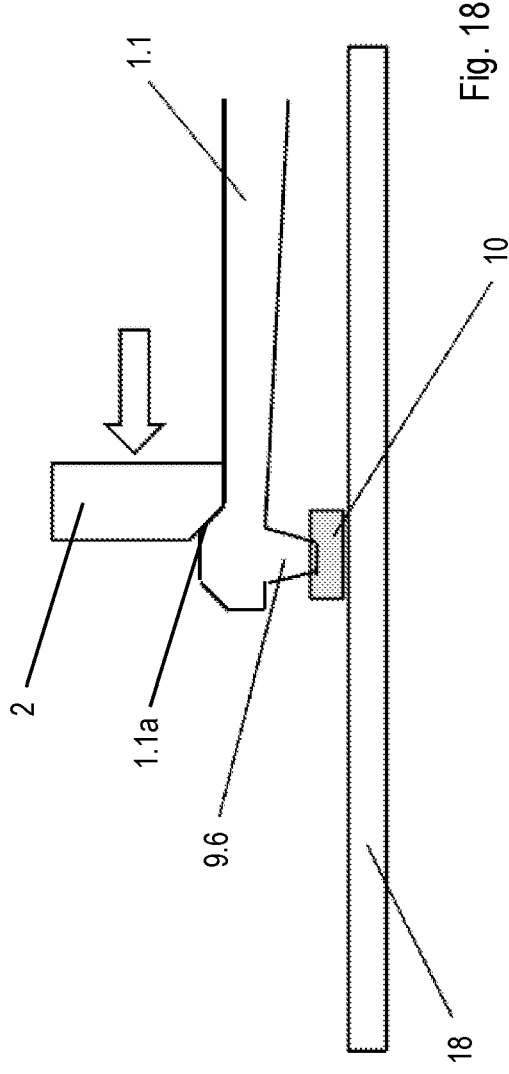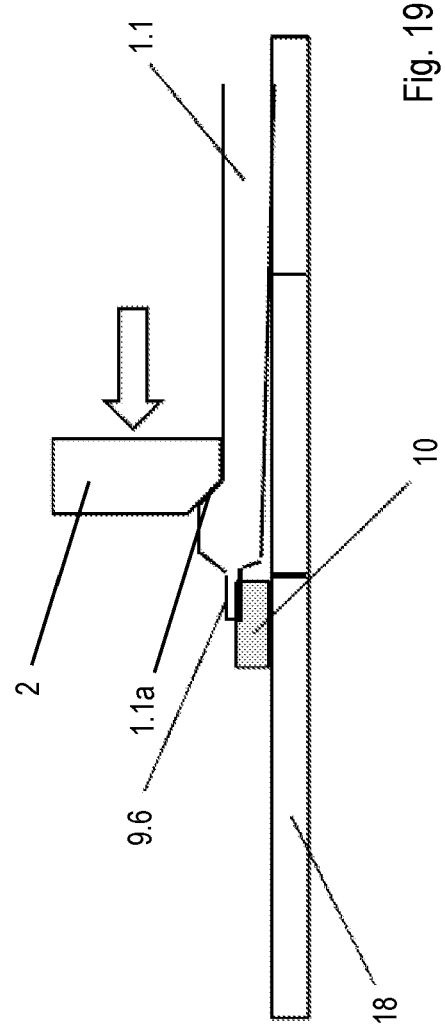

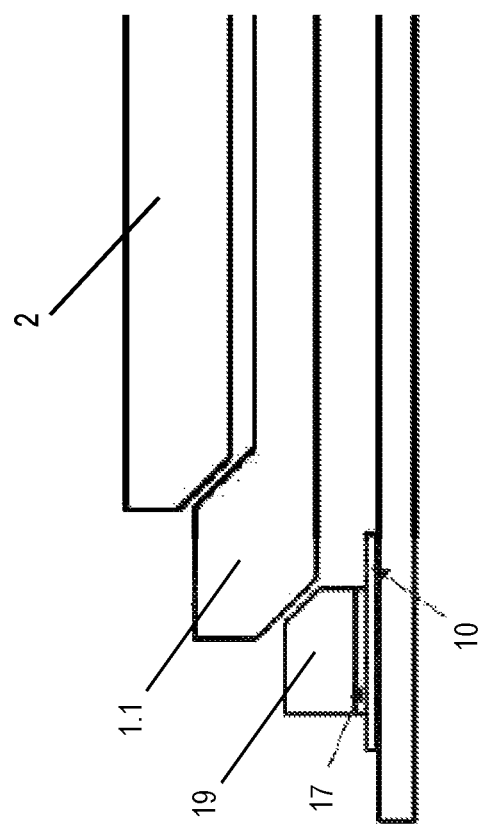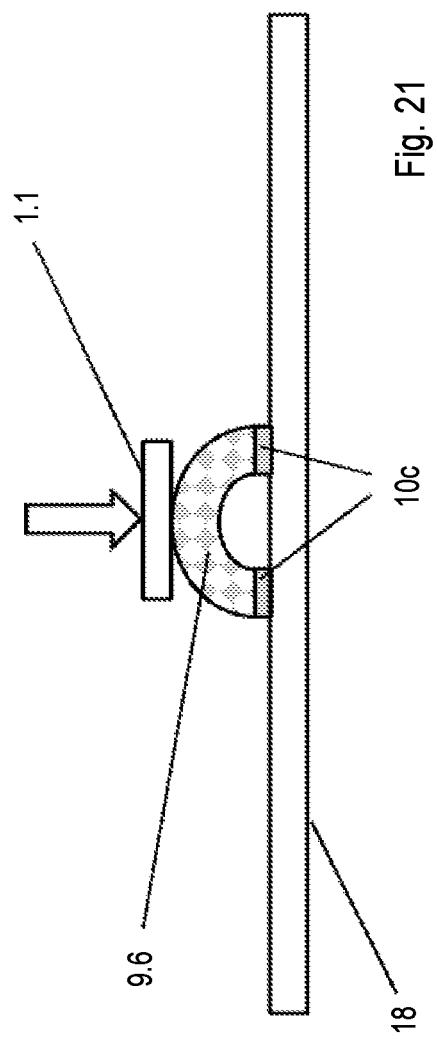

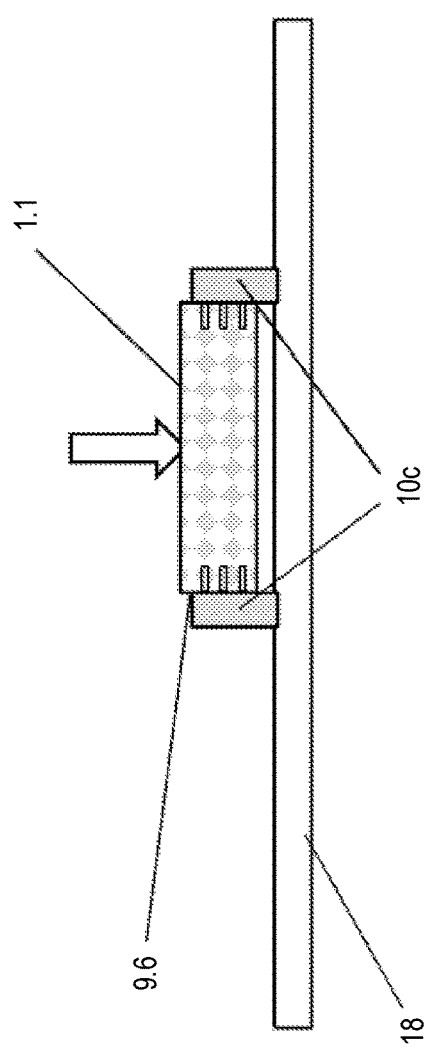
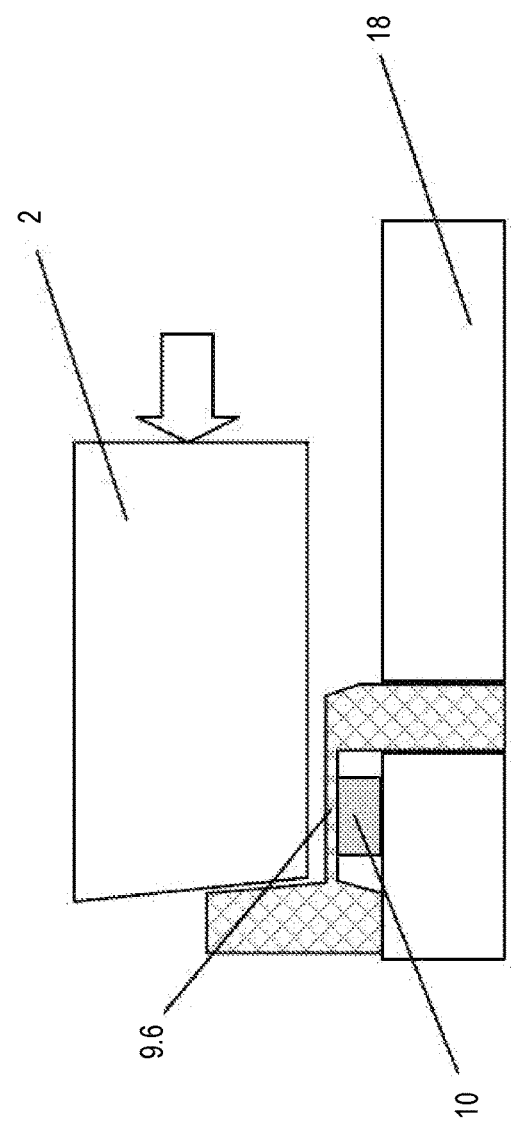

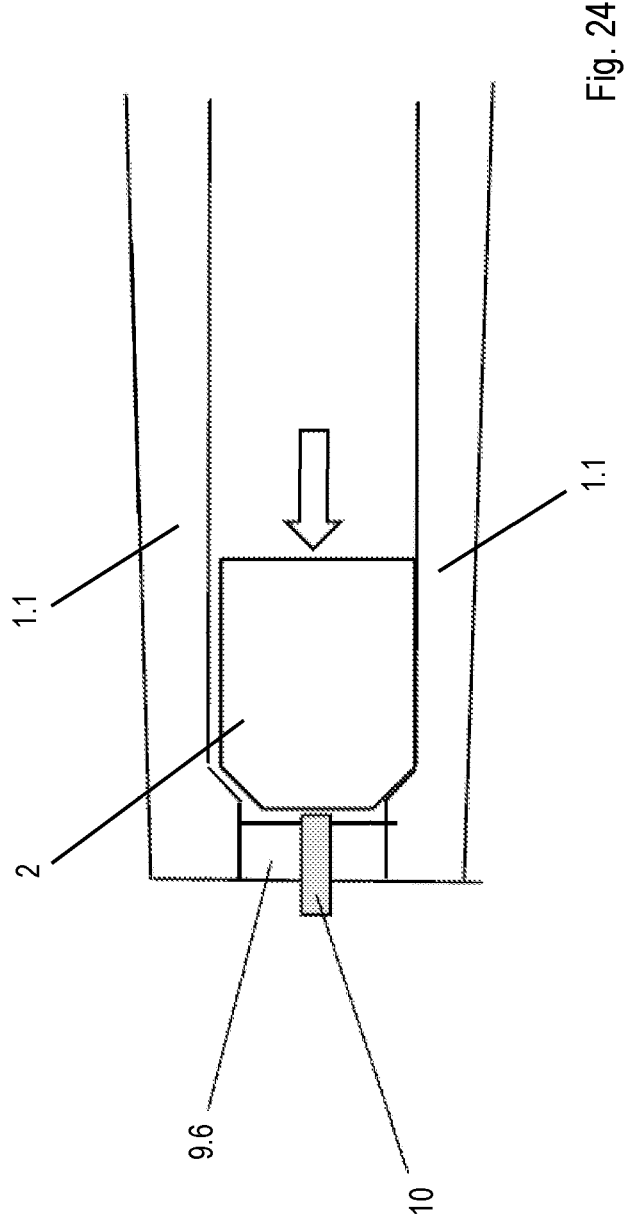

Table 1

| | | | 0.2 | No consideration of heat losses | | | | |
|---|---|---|---|---|---|---|---|---|
| Available Electrical Power | P | W | | | | | | |
| Starting Temperature | T_init | °C | 23 | | | | | |
| Plastics | | | PA | PBT 10% glass fibers | PMMA | PC | PET | ABS |
| Structure | | | Semi-crystalline | Semi-crystalline | Amorphous | Amorphous | Semi-crystalline (30-40%) | Amorphous |
| Volume (sample) | V | m3 | 3.0E-09 | 3.0E-09 | 3.0E-09 | 3.0E-09 | 3.0E-09 | 3.0E-09 |
| Density (medium) | ρ | kg/m3 | 1440 | 1450 | 1190 | 1200 | 1400 | 1030 |
| Mass (sample) | m | kg | 4.32E-06 | 4.35E-06 | 3.57E-06 | 3.60E-06 | 4.20E-06 | 3.09E-06 |
| Specific heat capacity (medium) | cs | J/(kgK) | 1200 | 1500 | 1500 | 1170 | 1500 | 1200 |
| Energy of fusion (medium) | H | J/kg | 213000 | 333000 | | | 145000 | |
| Heat of fusion (sample) | Qs | J | 9.20E-01 | 1.44855 | 0 | 0 | 0.609 | 0 |
| Melting temperature (semi-crystalline)/Glass-transition temperature (Amorphous) | T_melt | °C | 220 | 223 | 110 | 148 | 250 | 95 |
| Temperature difference | ΔT | °C | 197 | 220 | 87 | 125 | 227 | 72 |
| Heat absorption (up to TS) | Q | J | 1.02 | 1.31 | 0.47 | 0.53 | 1.43 | 0.27 |
| Energy for heating and melting | Qtot | J | 1.94 | 2.75 | 0.47 | 0.53 | 2.04 | 0.27 |
| Duration of energy supply until TS is reached | Δt_TS | s | 5.11 | 6.53 | 2.33 | 2.63 | 7.15 | 1.33 |
| Duration of energy supply until melting/softening is reached | Δt_melt | s | 9.71 | 13.77 | 2.33 | 2.63 | 10.20 | 1.33 |

Fig. 28

Table 2

| Material Designation | Material properties, mechanical | | | | Material properties, thermal | | | | Vicat | | | HDT | | ΔHDT |
|---|---|---|---|---|---|---|---|---|---|---|---|---|---|---|
| Type of plastic | Tensile Modulus MPa | Yield stress MPa | Behavior | Yield strain % | water absorption % | Tg | Specific heat capacity [J/kgK] | Thermal conductivity [W/mK] | Temperatures of the thermal data [°C] | Density [dg/m3] | A/Rate50 [°C] 10N | B/Rate50 [°C] 50N | B/Rate50 120 [°C] 50N | Method A flexural stress s=1.8Nm m²=const. | Method B flexural stress s=0.45 Nmm²=co nst. | Difference between HDT A and B [%] |
| ABS | 2400 | 46 | ductile | 2.6 | | | 1800 | 0.129 | 245 | 1040 | 102 | 99 | | 94 | 98 | 4.3 |
| ABS-GF | 5600 | 70 | brittle | 1.7 | | | | | | 1190 | | 105 | 106 | 104 | 107 | 2.9 |
| Cellulosic | 1448 | 31 | ductile | 0.45 | | | | | | 1200 | | | | 75 | 88 | 17.3 |
| Copolyester | 1585 | 44 | ductile | 7 | | 120 | 1576 | 0.208 | | 1170 | | | | 92 | 109 | 18.5 |
| MABS | 2000 | 48 | ductile | 4 | 0.7 | | 2060 | 0.155 | 245 | 1080 | | 93 | | 90 | 94 | 4.4 |
| PC-ABS | 2100 | 50 | ductile | 4.5 | 0.7 | | 1960 | 0.157 | 260 | 1110 | | 113 | 115 | 99 | 120 | 21.2 |
| SAN | 3700 | 72 | brittle | 3 | 0.2 | | | 0.17 | | 1080 | | 106 | | 86 | 99 | 15.1 |
| San-GF35 | 12500 | 96 | brittle | 1 | | | | | | 1350 | | 105 | | 98 | 101 | 3.1 |
| SMMA | 3300 | 60 | brittle | 2.5 | 0.1 | | 2300 | 0.21 | 246 | 1080 | | 98 | 105 | 80 | 90 | 12.5 |

Fig. 29

CANNULA INSERTION MECHANISM

CROSS-REFERENCE TO RELATED APPLICATIONS

This application claims priority to International Patent Application No. PCT/IB2018/059688, filed Dec. 6, 2018, entitled "CANNULA INSERTION MECHANISM" which in turn claims priority to European Patent Application No. 17209764.4 filed on Dec. 21, 2017, entitled "CANNULA INSERTION MECHANISM", each of which is incorporated by reference herein, in their entirety and for all purposes.

TECHNICAL FIELD

The present invention relates to a device for administering a substance, a liquid medical substance for example, which is discharged by means of a cannula that is inserted into a body. In particular, the invention relates to a mechanism for automatic insertion of a cannula, with which a cannula can be automatically inserted into a body by being ejected from an administration device or a cannula housing, for example. After penetration of the cannula into a body, a medicinal substance such as insulin can be discharged in a metered manner to the body by the cannula.

BACKGROUND

A syringe, also known as an injection pen or an infusion pump, is frequently used for administering a medicinal substance or fluid. An infusion pump can be connected to an infusion set or a catheter in order to discharge the substance in a metered manner. One possibility for controlled substance administration is the discharge to a patient by an external pump, which can be carried on the patient, for example, or glued onto the patient's skin, the substance being discharged from the external pump through a catheter inserted into the patient's body.

The introduction of a catheter or cannula can be done manually, for example, by means of an infusion set. As an alternative to manual setting of a cannula, the cannula may be automatically introduced.

U.S. Pat. No. 9,220,838 B2 discloses a cannula introduction device in which a cannula in a housing is preloaded by a first spring, the spring being prevented from relaxation and propulsion of the cannula by a retaining part. The retaining part is a rotatable lever to which a force in the release direction is applied by an additional, second spring. The rotatable retaining part is held in the blocking position against the force of the additional spring by an actuator, and after operation of the actuator and release of the retaining part, the retaining part is pulled by the additional second spring out of the blocking position into a release position so that the first spring can relax and effect the insertion of the cannula. In one embodiment, the actuator for retaining the blocking element against the force of the second spring can be a hook element which is connected to a meltable part, around which a wire, in the form of a heating coil for example, is wound. If an electric current flows through the wire, the meltable part melts so that the blocking element is rotated about an axis of rotation by the force of the second spring and functionally releases the first spring.

SUMMARY

Embodiments of the device according to the invention can offer one or more of the following advantages: A secure storage of the device, in particular a secure long-term storage. A secure triggering of the insertion, in particular for components subjected to pressure or tension for extended periods of time. Immunity with respect to accelerations of the type that could occur in case of a fall or an impact. A simple, automatic triggering of an insertion, by an actuation initiated by an electrical signal, for example. Increase in the assembly process safety. Reduction of the space requirement for the retaining or triggering mechanism.

References below to a cannula should be understood to mean both a single cannula, for example a soft cannula, or alternatively multi-element systems such as a hard cannula, a steel cannula or a needle, which are surrounded by a soft cannula (made from elastic polymer material for example). In the latter case, the soft cannula surrounding the hard cannula can be inserted along with the hard cannula during insertion into tissue and, after insertion, the hard cannula, which is movable relative to the soft cannula, can be pulled back inside the soft cannula out of the tissue, while the soft cannula remains in the tissue. A fluid which enters (proximally) the hard cannula at the end facing away from the insertion site (distal end) can pass through the hard cannula and exits at the distal outlet opening of the hard cannula into the interior of the soft cannula surrounding the hard cannula and is conducted by the soft cannula until it is discharged at the distal end of the soft cannula. The inner periphery of the soft cannula bears sealingly against the outer periphery of the hard cannula so that no fluid can pass through the region at which the hard cannula and the soft cannula contact one another. The hard cannula is also preferably movable inside the soft cannula, which is formed from a plastic or deformable material, for example. Both the soft cannula and the hard cannula are preferably flexible, i.e., can be bent or curved in the longitudinal direction. Alternatively, the hard cannula can be arranged outside the soft cannula, with an otherwise identical and sealing design.

According to a first aspect, the invention relates to an insertion mechanism for a cannula that can be constructed, for example, as a soft cannula, or as a hard cannula with a surrounding soft cannula as described above, or only as a hard cannula. The cannula is mounted movably relative to a cannula housing, so that the cannula can be accelerated relative to the cannula housing, for example, or automatically extended or ejected out of the cannula housing. The cannula housing can be a structure surrounding the cannula in part or completely and can have one or more openings, and the cannula can also be completely or partially guided outside the cannula housing, for example. The cannula is mounted on at least one cannula holder which can be displaced relative to the cannula housing in order thus to cause an extension or puncture of the cannula. The cannula holder(s) may be movable relative to the cannula housing, and in the cannula housing, for example, and can be displaced in a cannula advancing direction and a cannula retraction direction, and the puncture direction of the cannula can also deviate from or be different from the cannula advancing direction or the cannula retraction direction due to a cannula curvature. The at least one cannula connected to the at least one cannula holder can extend or be guided farther in the distal axial direction relative to the retaining point on the cannula holder and can also have one or more curvatures or bends, so that the cannula can be guided along or in a continuation of a displacement path of the cannula holder, for example in a straight line along the cannula housing and continuing in a curve and subsequently again in a straight line. At least one energy accumulator element for generating an insertion movement of the cannula holder, and thus generating an insertion movement of the cannula, can apply a force in the advancing or insertion direction to the cannula holder in order to be able to perform an automatic insertion after the triggering of the energy accumulator element. The energy accumulator element can, for example, be at least one preloaded compression spring, or also multiple parallel or serially arranged springs, for example, or alternatively also one or more tensile springs provided functionally between the cannula housing and the cannula holder and optionally can also be connected to one or both of these elements. The energy accumulator element can also be a different mechanical or hydraulic or pneumatic element or a magnetic, electromagnetic or electromechanical drive that can move the cannula holder relative to the cannula housing.

The energy accumulator is prevented by a blocking or retaining element (e.g., a triggering element) from discharging or relaxing or releasing the permanently acting force; the blocking or retaining element acts directly on the energy accumulator or indirectly on the energy accumulator, on the cannula holder for example, in order to prevent the energy accumulator or cannula holder in the blocked state from moving in the insertion direction. The blocking or retaining element can be constructed as a single element, e.g. a spring arm, or can be composed of two or more partial elements, e.g. two or more spring arms, which can jointly or individually secure or block the insertion device, such as an insertion energy accumulator, i.e., prevent a discharge and energy transfer. The blocking or retaining element can also have a mechanical step-up or step-down function and be configured as a reduction gear, for example, for reducing or lowering the force to be retained. A reduction gear can have a single-stage, two-stage or multi-stage design and have gears and/or threaded elements for implementing the step-down function. A fusible, softenable or weakenable safety element for securing the blocking or retaining element can likewise be provided doubly or multiply in order to secure the corresponding number of blocking elements. This softening or weakening can be brought about by increasing the temperature, for example. It is not absolutely necessary for the material to become fluid. For example, when the glass transition temperature Tg is exceeded, a solid amorphous material or solid glass or polymer transitions into a rubber-like or viscous condition to remove the blocking or retaining function.

According to an optional embodiment for example, the blocking or retaining element can be constantly subjected to a force from the insertion energy accumulator, which presses the retaining element into the release position, so that the retaining element must be held in the blocking position by a safety mechanism in order to prevent triggering cannula insertion. The retaining element or holding element can be a lever, for example, or in general a structure on which the force of the insertion energy spring acts in the safety and non-triggered state, wherein the safety mechanism can be pushed out of the blocking position, without a further drive such as an additional spring, merely by the force of the insertion energy accumulator, in order thus to release or initiate the cannula insertion process if the retaining element or the holding element were not secured by the safety mechanism, which holds the retaining element in the blocking position. The insertion process thus can be performed with only a single energy accumulator, for example, such as a single insertion spring, which firstly provides the energy for the insertion, i.e., the advancement of the at least one cannula, and secondly provides the energy for pressing the retaining element out of the retaining position after the safety mechanism has released the retaining element, i.e., for a movement of the retaining element out of the blocking position into a release position by the pressure of the insertion spring. Alternatively, it is also possible that a force is not applied to the blocking or retaining element by the insertion energy accumulator. Optionally, an additional energy accumulator or an additional spring can be provided for this purpose as disclosed in U.S. Pat. No. 9,220,838 B2, for example.

The safety element, which holds the retaining element or trigger element of the insertion energy accumulator in the blocked position and prevents the deflection thereof to release or perform insertion, can consist of or be constructed from a fusible, breakable, softenable or weakenable material, such as a plastic element or a solid glass or polymer, which can be electrically nonconductive or, alternatively, electrically conductive. The solid glass, the solid amorphous material or the polymer can transition into a rubber-like to viscous state if the glass transition temperature Tg is exceeded. It is not absolutely necessary that a melting temperature be reached. According to one embodiment, the fusible, softenable or weakenable material can be under tensile stress, caused by the insertion energy accumulator, for example, which presses directly or indirectly on the retaining element that is coupled or connected to the safety or the element that can be melted, softened or weakened.

The at least one safety element can be integrally and/or form-fittingly connected to the retaining element or elements or triggering element or elements. An integral connection enables a simple and secure construction as well as a secure long-term retention of the insertion energy accumulator.

On the weakenable or fusible element or in the vicinity thereof, at least one warming or heating element is provided, such as a heating wire, heating coil or heating surface, which generates heat when current flows, for example, in order to completely or at least partially soften or melt the fusible element by heating it. If the ability of the fusible or weakenable element to restrain a tensile, compressive or shearing force is attenuated due to heating, or it is fully melted or severed, e.g., divided at one point, this releases the coupled retaining element so that the insertion energy accumulator can move the no-longer-secured at least one cannula holder relative to the cannula housing and thus begin the insertion movement. To trigger the insertion, it is not necessary that the fusible or softenable element be melted completely, because the restraining capability of an element under tensile stress, for example, need only be attenuated sufficiently that an applied tensile force can no longer be restrained and a retaining end of the fusible or softenable element can move or shift to such an extent that a retaining element is brought from a blocking position into the release position. It can be possible that the softenable or fusible element is softened by heating, for example, and an extension or even severing or tearing of the fusible element is only effected by the force of the injection energy accumulator acting on the fusible element. Complete severance of the softenable or fusible element, which can also be referred to as a fusible safety element, is not absolutely necessary, however.

The fusible or softenable element or fusible safety element is provided fixedly at one side, for example, on or immovable relative to the cannula housing, and attached to a fusible safety holder for example. At the end of the fusible safety element opposite the holder, the fusible safety element can be coupled to a blocking or retaining element of the energy accumulator, which optionally is itself subjected by the insertion energy accumulator to a force that can press the blocking or retaining element out of the blocking position into a release position, so that this force can act on the fusible safety element as a tensile force or a compressive force. The safety element can also be loaded in two opposing directions, by two spring arms, for example.

According to an additional embodiment, the fusible safety element can include or consist of a material that is electrically conductive (i.e. has a suitable electrical resistance) and softenable or fusible, which is coupled as described above for the fusible safety element to the blocking or retaining element of the insertion energy accumulator and is loaded with a tensile force or, alternatively, a compressive force, for example. To trigger the insertion, i.e. to release the blocking or retaining element by movement of the fusible safety element or a part or end thereof, caused by softening or melting, an electrical voltage can be applied by which a current flows through the softenable or fusible and electrically conductive material, such as an electrically conductive plastic or an easily softenable metal, and thereby causes heating.

If a safety element that holds a blocking or retaining element of the insertion energy accumulator in the blocking position is under tensile stress, it can be formed as a flat or rod-shaped element, and can have a narrowed area or a designed separating point which is easy to extend or sever with the lowest possible energy expenditure, for example.

According to another aspect of the invention, the blocking or retaining element of the insertion energy accumulator is secured by using a softenable or fusible element that is under compressive stress. The retaining element, which tends to move from the blocking position into the release position due to the pressure (or alternatively due to the tensile force) of the insertion energy accumulator, is held in the blocking position or pressed into the blocking position by a softenable or fusible element. The element securing the blocking or retaining element consists at least in part or entirely of a softenable or fusible material such as plastic or metal, which is softened or caused to at least partially melt by heating. This material is arranged between the blocking or retaining element pressing on this material and an opposing pressure point or support point opposite the contact point with the retaining element in such a way that the securing material, which is provided fixedly on or in or immovable relative to the cannula housing, is supported on the supporting point. The securing material is preferably guided in a region between the contact with the blocking or retaining element on the one hand and the support point on the other in such a way that it could move aside if the support point were not present or if the length of the securing material were shortened. A shortening of the length of the securing material can be achieved, for example, by heating the securing material at least in part or completely by means of a warming or heating element at the region of the support point and/or in the region between the support point and the retaining element. Due to heating of the securing material, it can be softened at the heating point, in the region of the support point for example, such that it yields or melts under the compressive stress originating from the blocking or retaining point, caused for example by the insertion spring, and yields to the applied pressure. With a sufficient heating or melting, the securing material yields against the pressure of the blocking or retaining element sufficiently that the retaining element can move from a blocking position into a release position, which can be accomplished by the pressure of the insertion energy accumulator, for example. It is not necessary in this case that the entire securing material is softened or melted. It is sufficient in principle if the supporting capacity of the securing material is attenuated by a softening or melting process or if the length thereof is reduced sufficiently that the blocking or retaining element pressing against the securing material can no longer be held in the blocking position by the securing material.

According to an additional aspect, a securing material can be used which is subjected to pressure by the blocking or retaining element of the insertion energy accumulator and presses against an opposing pressure point or support point, which is preferably fixed relative to the housing or cannot be moved relative to the insertion housing. The securing material can be regarded as a tappet, for example, which presses onto a release element on the side opposite the blocking or retaining element. The tappet can be mounted displaceably between the contact points for the blocking or retaining element and those for the release element, so that the tappet is pressed onto the release element under a pressure originating from the blocking or retaining element and cannot escape to the side. The release element can be formed as a softenable or fusible element, in the form of a plastic or metal that is softenable or fusible by heat and/or it can be formed as an electrical resistance element which gradually loses the ability to exert mechanical opposing pressure on the tappet when it is heated or melted or when a current flows through it. A current for release can flow through the tappet and it can thus be softened or de-soldered or the solder can be broken, because the flowing current leads to a heating and melting of the material or of a solder that has been used, so that the tappet cannot exert any retaining force generated by an opposite pressure point against the pressure force of the blocking or retaining element, whereby the blocking or retaining element displaces the tappet and thus allows the discharge of the insertion energy accumulator. The tappet can pass through the point at which the release element was present prior to the triggering, i.e. prior to de-soldering or soldering breakage.

According to another aspect, the securing of the blocking or retaining element of the insertion energy accumulator against a deflection is implemented by means of a sheet-like element or film element. The sheet-like element or the film can be applied over the blocking or retaining element in such a way that the film can restrain the force of the retaining element acting in the release direction. For example, the film can be applied or adhered over the retaining element and at least two adjoining regions, e.g., on a surface of the cannula housing, such that the retaining element cannot reach the release position so long as the film is present or tensioned, because the film is located at the position that the retaining element would occupy in the release position. The film thus absorbs the pressure of the blocking or retaining element and holds it in the blocking position. For example the film can be fastened to the cannula housing or the cannula holder in order to hold the retaining element in the blocking position. According to one variant, the film can also be provided in the form of separate single film elements which retain two or more retaining elements in that the film or film elements are applied or glued or stretched over the retaining elements in such a way that the retaining elements cannot reach the release position.

The description below is made for simplification on the basis of examples for one retaining element and one safety element, although two, three or more retaining elements can also be provided in a specific embodiment of the invention, which are retained by one, two, three or more safety elements, without this being expressly repeated.

To release the blocking or retaining element, the film can be heated in order thereby to no longer be able to restrain the release force of the retaining element caused by the insertion spring, so that the blocking element can pass through the film, for example, or can lead to a stretching or tearing of the film, whereby the blocking or retaining element can reach the release position. For this purpose, one or more heating elements can be provided on the film or in the vicinity of the film in order to appropriately weaken or soften to cause the film to tear due to heating. For example, the film can have a tapered region which can be heated by a heating element in order to achieve an opening or tearing of the film.

According to a further aspect, an insertion mechanism for a cannula has a cannula housing as well as a cannula holder movable relative thereto, to which cannula holder a force that acts in the direction in which the cannula holder can move relative to the cannula housing can be applied by an insertion energy accumulator. In general, the reader is referred to the above explanations of the design for the insertion mechanism and the components thereof, although in the present embodiment, no blocking or retaining element for retaining the cannula holder relative to the cannula housing as above is provided. Instead, the cannula holder is retained in the fixed position relative to or on the cannula housing by means of an adhesive or adhesive surface. The release or triggering for insertion can be performed by a heating element which is provided on or at the adhesive point or the adhesive, and the adhesive can lose its adhesiveness by heating for example, whereby the cannula holder is released so that it can be displaced relative to the cannula housing by the force of the injection energy accumulator. Alternatively or additionally, an adhesive can be used that is conductive, so that for release, an electric current can be applied to the conductive adhesive, flowing through the adhesive and leading to a heating of the adhesive due to the intrinsic internal resistance of the adhesive and thus to the reduction of adhesive force and consequently to the release of the cannula holder in the cannula housing.

According to another aspect, the invention relates to an administration device for administering a substance using an insertion mechanism as described above and having a reservoir for the substance, and/or having a pump which is connected to the proximal end of a cannula. At this connecting point, the cannula can be a hard cannula and a soft cannula as described above and can also be connected to the reservoir by means of a comparatively soft tube. Thereby loss forces that can arise during bending of the steel cannula can be reduced.

According to another aspect, the invention relates to a method for automatic injection or advancement of a cannula by using an insertion mechanism as described above. The method can be performed without the cannula that has been advanced or pushed out of the cannula housing penetrating into tissue, and relates in general only to the triggering process or release process of the cannula prior to an optional later insertion or non-insertion. The method comprises the steps of heating a safety structure, whereby it is weakened, for example, or caused to melt or deform or generally release a safety position, whereby a retaining element for retaining a cannula holder against the force of the insertion energy accumulator can be released.

Considered in general, the invention relates to the release or triggering of an insertion mechanism by softening according to one embodiment, which can be achieved, for example, by heating a material. For this purpose, a safety mechanism or safety element can be used which is under compressive stress, for example, or on which a shearing force is acting or which is under tensile stress, and combinations of these stresses can be present, such as pressure and shearing.

According to one embodiment, a medium under pressure, as shown in the subsequent embodiments according to FIGS. 10A to 10O and 11A to 11O for example, can be softened or melted by supplying heat so that it no longer withstands a (retaining) stress and moves aside. This mechanism can be used in order to shift an additional mechanism, such as a retainer for a triggering element or retention element, irreversibly from a blocked into a released state.

Embodiments in which a safety element is under compressive stress, for example, have the advantage that a cross section is not critically stressed during a long, e.g. multiyear, storage time.

Less material or less volume has to be heated for a securing element under tensile stress because the stress in the material becomes greater the smaller the cross section is, which simplifies a secure releasing or opening of the safety element.

BRIEF DESCRIPTION OF THE DRAWINGS

The invention will be explained in detail below with reference to embodiments.

FIG. 1A shows a sectional view of a two-spring insertion mechanism in the initial state;

FIG. 1B shows the insertion mechanism shown in FIG. 1A viewed from above;

FIG. 4 shows an exploded view of the components of the insertion mechanism;

FIG. 5 shows a perspective view of the insertion mechanism with a blocking or triggering element;

FIG. 6 shows a top view of the insertion mechanism to illustrate the blocking element;

FIGS. 7A and 7B show sectional views of the insertion device while releasing the coupling of the soft cannula holder and the hard cannula holder prior to retraction of the steel cannula;

FIGS. 8A to 8O show a first embodiment of an automatically releasable safety mechanism;

FIGS. 9A to 9O show a second embodiment of an automatically releasable safety mechanism;

FIGS. 10A to 10O show a third embodiment of an automatically releasable safety mechanism;

FIGS. 11A to 11O show a fourth embodiment of an automatically releasable safety mechanism;

FIGS. 12A to 12O show a fifth embodiment of an automatically releasable safety mechanism;

FIGS. 14 to 18 show embodiments with safety element under compressive stress;

FIGS. 19 and 20 show embodiments with a combined compressive and shear stress;

FIGS. 21 and 22 show embodiments with combined blocking and heating elements;

FIGS. 23 to 25B show embodiments with safety elements under tensile stress;

FIG. 28 shows in Table 1 an example a selection of plastics and the corresponding period to melt or soften a defined volume of plastic (without taking losses into consideration); and FIG. 29 shows in Table 2 a list of plastics that may be used in the safety mechanism of the present disclosure.

In FIGS. 8A to 13O, the partial Figures A to E designate views of the respective embodiment in the initial state with an intact safety mechanism or element, partial Figures F to J show the condition after releasing the safety mechanism or element and the subsequent advancement of the cannula, and partial Figures K to O show views of the insertion mechanism with an extended soft cannula and retracted hard cannula.

DETAILED DESCRIPTION

Figure 3:
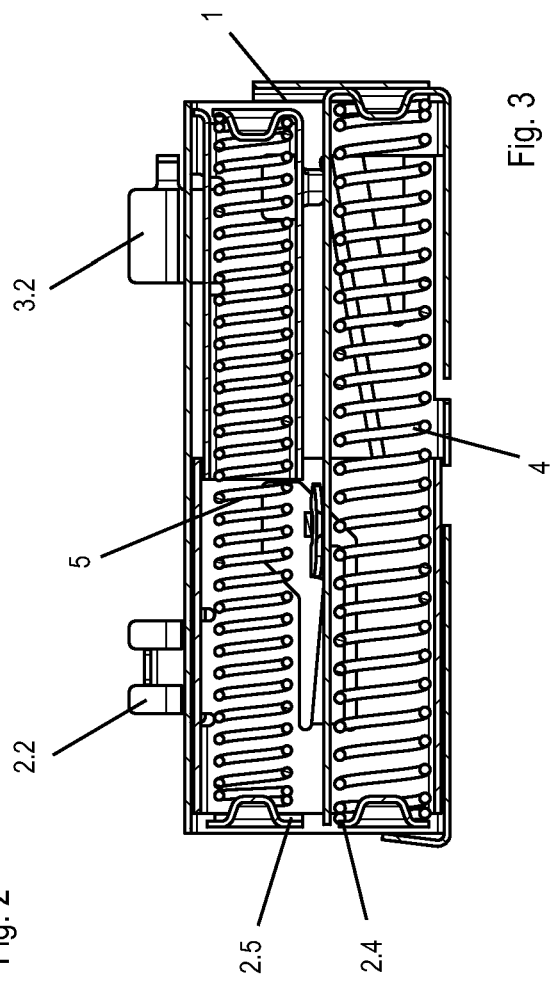
FIG. 3 shows the insertion mechanism with an extended soft cannula and a retracted steel cannula.

FIG. 1A shows a two-spring insertion mechanism in a sectional view with displacement-dependent process control. The insertion mechanism in the described embodiment is designed as a cannula insertion and retraction mechanism, and after triggering, it can automatically advance a steel or hard cannula 8 together with the soft cannula 7 surrounding this steel or hard cannula 8, and after the advancement process has taken place, can retract the hard cannula 8 inside the soft cannula 7 while the extended soft cannula 7 remains in the extended state. If the cannula 7, 8 has been applied to a body prior to advancement, for example, an automatic insertion or puncturing process can thus be achieved. The soft cannula 7 is mounted or guided non-displaceably on a mount or guide 2.2 of a soft cannula holder 2, which is shown in the exploded view of FIG. 4 and can be displaced relative to the cannula housing 1 and, together with a relative movement of the soft cannula holder 2, can also be displaced relative to the cannula housing 1. The hard cannula 8 is secured or guided on a hard cannula mounting 3.2 or hard cannula guide and thus moves together with the hard cannula holder 3.

The soft cannula holder 2 is movable inside the cannula housing 1 in the longitudinal direction along the insertion finger 1.2 likewise provided in the interior of the cannula housing 1 and also serving as a guide (e.g., reverser guide) and process control. The soft cannula holder 2 has, at the end face thereof, shown at the left in FIGS. 1 to 7 and facing in the insertion direction of the soft cannula holder 2, a stop or a contact surface 2.4 for an insertion spring 4, and a contact surface or a stop 2.5 for the hard cannula holder 3, which stops are spaced apart from one another by an opening 2.3 for passage of the insertion finger 1.2. On the soft cannula holder 2, the mount or guide 2.2 for the soft cannula 7 is provided and is connected fixedly and non-displaceably to the soft cannula holder 2 and holds the soft cannula 7 preferably fixedly and non-displaceably, so that in case of a relative movement or displacement movement of the soft cannula holder 2 relative to the cannula housing 1, the soft cannula 7 carried by the soft cannula holder 2 is likewise displaced relative to the cannula housing 1. For example, the soft cannula 7 can be fixed by means of clamping elements to the mount or guide 2.2 and/or fixed by an adhesive to the mount or guide 2.2. The mount or guide 2.2 should be constructed such that the soft cannula 7 can be carried along in a movement of the mount or guide 2.2 or a movement of the soft cannula holder 2, wherein the soft cannula 7 is provided or fixed in the mount or guide 2.2 such that a substance can pass through the interior of the soft cannula 7 in the holding state. In the initial position, a hard cannula 8 is provided inside the soft cannula 7 over the entire length thereof and protruding at the ends, which hard cannula is displaceable inside the soft cannula 7 in the longitudinal direction thereof and can carry the soft cannula 7 during an advancement process or insertion process or move together with the soft cannula 7.

The soft cannula holder 2 has a coupling or triggering element 2.1 (FIG. 4) which, in the initial state, brings about the coupling between the soft cannula holder 2 and the hard cannula holder 3, such that soft cannula holder 2 and hard cannula holder 3 cannot be displaced relative to one another or can be displaced only to a limited extent. A movement carried out by the soft cannula holder 2, such as an insertion movement, is transferred by the soft cannula holder 2 to the hard cannula holder 3 by means of the coupling or triggering element 2.1, which initially serves as a coupling element. If the soft cannula holder 2 is moved in the insertion direction (to the left in the figures), then this movement is transferred by the coupling or triggering element 2.1 to the hard cannula holder 3, where the coupling or triggering element 2.1 engages with a mating coupling element or a tongue 3.1. In the single view of the soft cannula holder 2 in FIG. 4, the coupling or triggering element 2.1 is in an inward-folded and decoupled state. If the soft cannula holder 2 is inserted into the cannula housing 1 such that the process control or the insertion finger 1.2 passes through the opening 2.3 of the soft cannula holder 2, i.e., if it is inserted into the cannula housing 1 at the end face in the direction to the left as shown in FIG. 4, then in the anterior, narrower decoupling region 1.2a of the process control or insertion finger 1.2 shown at the left in FIG. 4, the coupling or triggering element 2.1 is folded inward because the process control or insertion finger 1.2 is narrower or tapered in the front region. In the rear, wide coupling region 1.2b (FIG. 6), the coupling or triggering element 2.1 is pressed outward by the process control or insertion finger 1.2, which is broadened or wider in this region, and is thus coupled to the mating coupling element or tongue 3.1 of the hard cannula holder 3, whereby the soft cannula holder 2 and the hard cannula holder 3 are non-displaceable relative to one another, so long as the coupling or triggering element 2.1 is in the wide coupling region 1.2b of the process control or insertion finger 1.2, which region is broadened and presses the coupling or triggering element 2.1 into engagement with the mating coupling element or tongue 3.1. In the tapered or narrower decoupling region 1.2a of the process control or insertion finger 1.2, the coupling or triggering element 2.1 can escape to the inside and is decoupled from the mating coupling element or tongue 3.1, whereby the coupling between soft cannula holder 2 and hard cannula holder 3 is released and both can be moved relative to one another or displaced independently of one another.

The hard cannula holder 3 has a guide or hard cannula mounting 3.2 for the hard cannula 8 which passes completely through the soft cannula 7 in the initial state shown in FIGS. 1A and 1B and is surrounded thereby, so that the hard cannula 8 both protrudes at the distal end from the soft cannula 7 and preferably has a slope or point at the distal end, and likewise protrudes out of the soft cannula 7 at the opposite, proximal end and is fastened fixedly and non-displaceably on the hard cannula mounting 3.2 of the hard cannula holder 3.

FIG. 1B shows a plan view onto the insertion mechanism shown in FIG. 1A, from which it is clear that the proximal end of the hard cannula 8 is connected to a cannula element 8.1 drawn in an arc shape, or continues as this cannula element, which can be connected, for example, to a reservoir 11 of the dispensed substance and/or a dispensing mechanism such as a pump. The loop-like structure of the cannula element 8.1 shown in FIG. 1B can ensure that the side of the loop-like structure of the cannula element 8.1 shown at the right in FIG. 1B can remain stationary relative to the cannula housing 1 and can be fixed thereon, for example, and the hard cannula 8 can be displaced in the distal direction thereof without a tensile force relative to or on the cannula housing 1 arising at the fastening point of the cannula element 8.1 (proximal region of the cannula element 8.1). In the opposing, distal region of the cannula element 8.1, it can move together with the hard cannula 8, and in a movement of the hard cannula 8 to the right in FIG. 1B, this results in a widening of the loop- or arc-shaped cannula element 8.1 as shown.

In the initial state shown in FIG. 1A, an insertion spring 4, which is designed as a compression spring, is braced at the proximal end of the insertion mechanism on the cannula housing 1 and, at the opposite end, on the stop or contact surface 2.4 of the soft cannula holder 2. The soft cannula holder 2 is thus pressed by the insertion spring 4 relative to the cannula housing 1 in the advancement direction or insertion direction of the cannula, and is held in position by a blocking or triggering element 1.1, which is a movable or deflectable component of the cannula housing 1. According to one embodiment, the blocking or triggering element 1.1 can be designed such that it is pressed by the pressure generated by the insertion spring 4 out of the blocking position into a release position, or would be if the triggering element 1.1 were not held in the blocking position shown by a safety mechanism or safety element, to be described below. For example, the blocking or triggering element 1.1 can be formed such that, directly by the insertion spring 4 or by the soft cannula holder 2 or optionally also by the hard cannula holder 3 in the blocking position, a force is applied via a drive face or slope 1.1a, e.g., bevel or a functional surface, such that the triggering element 1.1 is subjected to a force in the direction of a release position.

In the embodiment shown, the triggering element 1.1 of the cannula housing 1 engages in front of an end face of the soft cannula holder 2 and holds the soft cannula holder 2 in the rear, proximal position against the tension of the insertion spring 4, as shown in FIGS. 5 and 6 for example. In the example shown in FIG. 6, the drive face or slope 1.1a, e.g., functional surface, of the triggering element 1.1 undergoes a force in the pressure direction of the insertion spring 4, which has the effect that the triggering element 1.1 is pressed in the direction shown by the arrow P, i.e., in the direction toward the outer side of the cannula housing 1, for example, perpendicular to or transverse to the operative direction of the insertion spring 4, in order thereby to release the holding force on the soft cannula holder 2 from the triggering element 1.1 and thus release the soft cannula holder 2 so that the soft cannula holder 2, driven by the force of the insertion spring 4, which is braced against the cannula housing 1, can be moved or pushed in the insertion direction once the triggering element 1.1 has been released, because the safety mechanism that holds the triggering element 1.1 in the blocking position has been released or opened.

Figure 2:
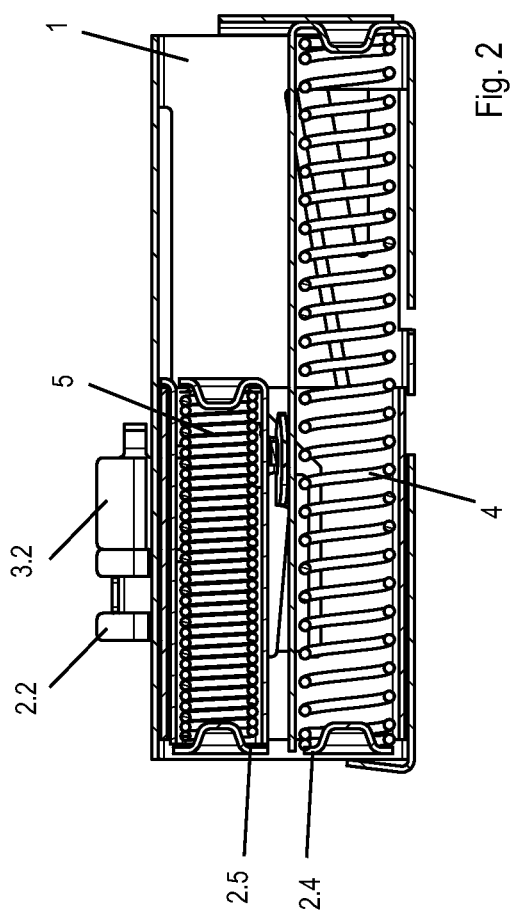
FIG. 2 shows a sectional view of the insertion mechanism with extended soft and steel cannulas.

After the release of the soft cannula holder 2, the insertion spring 4 presses the soft cannula holder 2 in the distal direction of the cannula housing 1, as shown in FIG. 2, until the soft cannula holder 2 reaches a front stop position of the cannula housing 1 inside the cannula housing 1. During this advancement or insertion movement, the soft cannula holder 2 carries the hard cannula holder 3 due to the coupling of the coupling or trigger element 2.1 to the mating coupling element or tongue 3.1 of the hard cannula holder 3, and displaces the latter in the distal direction relative to the cannula housing 1. During this joint movement of the soft cannula holder 2 and the hard cannula holder 3, the soft cannula mounting 2.2 and the hard cannula mounting 3.2 are displaced relative to the cannula housing 1 in the distal direction, as is likewise shown in FIG. 2, whereby the soft and the hard cannula 7, 8 are jointly pushed in the distal direction. If the cannula housing 1, and more particularly the distal tip of the hard cannula 8, is applied to a skin surface, a puncturing or insertion process can take place. It goes without saying that this functional process can also be carried out without an insertion taking place, for example in order to check the functionality of the insertion device. FIG. 2 shows the state of the insertion mechanism with soft and hard cannula 7, 8 extended and inserted, for example.

The retraction spring 5 is braced at one end against a contact or stop surface 2.5 of the hard cannula holder 3 and is designed in the embodiment as a tensioned compression spring that presses against or contacts a support or stop surface of the hard cannula holder 3 at the opposite support point.

In the state shown in FIG. 2, the coupling or triggering element 2.1 (see, e.g., FIGS. 7A and 7B) of the soft cannula holder 2, which engages with the mating coupling element or tongue 3.1 (see, e.g., FIG. 4) of the hard cannula holder 3, has been released from the coupled position, in which this coupling or triggering element 2.1 is held or pressed by the wide coupling region 1.2b (FIGS. 6 and 7A) of the process control or guide or insertion finger 1.2 of the cannula housing 1, because the mating coupling or triggering element 2.1 is situated in the distal region of the cannula housing 1, where the process control or insertion finger 1.2 is tapered or narrow, so that the coupling or triggering element 2.1 can fold in the direction toward the housing interior in the embodiment shown (see FIGS. 7A and 7B) and thus enables a decoupling from the mating coupling element or the tongue 3.1 of the hard cannula holder 3. In this way, the hard cannula holder 3 is decoupled from the soft cannula holder 2 and can move relative thereto.

Thereby the retraction spring 5 can relax, and as shown in FIG. 3, presses the hard cannula holder 3 back in the proximal direction until it bears against a stop surface of the cannula housing 1. This displaces the hard cannula mounting 3.2 relative to the soft cannula mounting 2.2, whereby the hard cannula 8 is displaced relative to the soft cannula 7 and retracted inside the latter. In the case of an optional insertion, the soft cannula 7 would remain inserted while the hard cannula 8 would be pulled back out of the puncturing point.

The decoupling between the soft cannula holder 2 and the hard cannula holder 3 takes place when, during the distally directed insertion movement of the soft cannula holder 2, the coupling or triggering element 2.1 reaches the region of the changeover geometry or tapering of the process control or insertion finger 1.2, i.e., the transition from wide coupling region to the narrow decoupling region 1.2b to 1.2a, whereby the coupling or triggering element 2.1 is pressed or pulled, by the force of the retraction spring 5 for example, from the holding position in the mating coupling element or tongue 3.1 of the hard cannula holder 3 into a release position.

The soft cannula 7 is arranged coaxially and sealingly over the steel or hard cannula 8. The tip of the steel cannula or hard cannula 8, which is sharpened for example, protrudes a few millimeters out of the soft cannula 7 in order to allow the smoothest and most pain-free possible puncturing of the skin. The steel or hard cannula 8 and soft cannula 7 are moved simultaneously to the injection point for puncturing. After having reached the injection depth, which can be the case in the state of the insertion mechanism shown in FIG. 2, the soft cannula 7 is fixed in the anterior or distal position, by means of a snap connection or retaining device such as one or more snaps or hooks, for example, or is held by the force of the relaxed insertion spring 4 in the anterior position. The steel or hard cannula 8 can then be pulled out of the insertion point or withdrawn relative to the soft cannula 7. A coaxial and sealing overlap between hard and soft cannula 8 and 7 remains. The optional subsequent administration of a fluid is done from a reservoir and/or a pump via the hard cannula 8 to the soft cannula 7 into the injection point.

The soft cannula 7 is guided through a cannula guide 6 which is attached to the cannula housing 1 fixedly relative to the housing 1 for example, wherein the soft cannula 7 can be pushed through the cannula guide 6 relative to the guide 6. The cannula guide 6 can be arranged such that the distance from the coupling or triggering element 2.1 of the soft cannula 2 is reduced during actuation.

Optionally, one or more coupling or triggering elements 2.1 having the same functionality as described above can be provided in addition to the above-described coupling or triggering element 2.1, in order to make the securing or blocking of the soft cannula holder 2 against the force of the spring 4 in the initial position more secure or more reliable.

The remaining tension of the insertion spring 4 and the retraction spring 5 has the effect that the soft cannula holder 2 and the hard cannula holder 3 are retained in their respective end positions (see FIG. 3).

Although the invention is described on the basis of the above embodiment using a two-spring mechanism, it can in principle also be used with a one-spring mechanism. A one-spring injection mechanism is known, for example, from Swiss patent applications 00061/17, 00063/17, 00062/17 and 00208/17, the disclosures of which are incorporated herein by reference. Therein a soft and steel cannula can be pushed out of an insertion device and inserted, driven by a single spring, and after insertion has been accomplished, the spring may not be completely relaxed and can be re-coupled by a drive mechanism so that the hard cannula can be pulled out of the soft cannula with the residual spring energy.

In place of a two-spring mechanism, for example, four springs can also be provided by arranging two springs in serial or parallel for each movement direction. In that way, a flatter characteristic curve can be realized for a serial arrangement, or a flatter characteristic curve and a higher final force can be realized with a parallel arrangement.

Figure 8L:
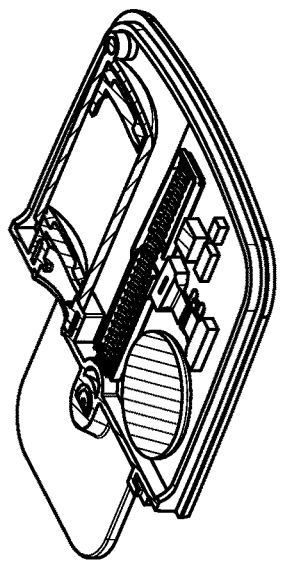
Figure 8K:
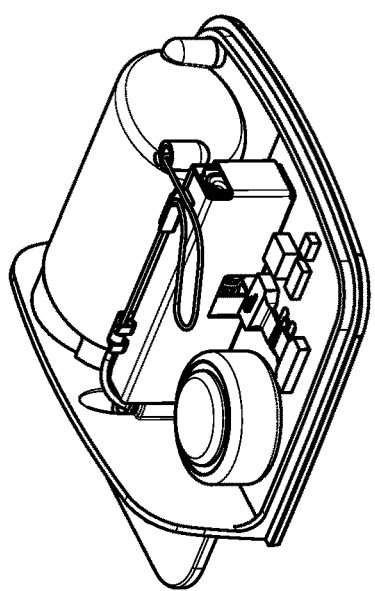
Figure 8O:
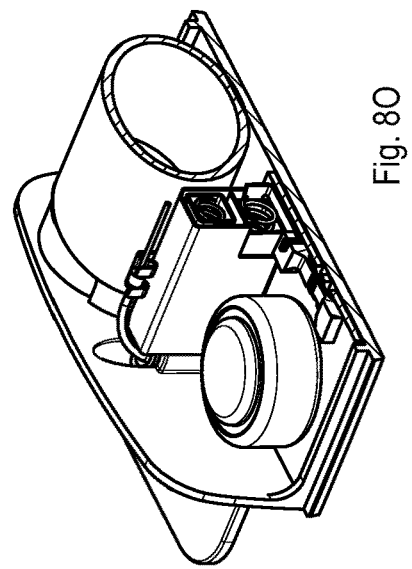
Figure 8N:
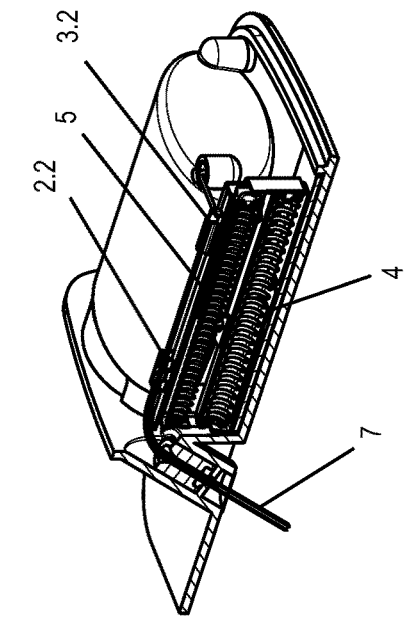
Figure 8M:
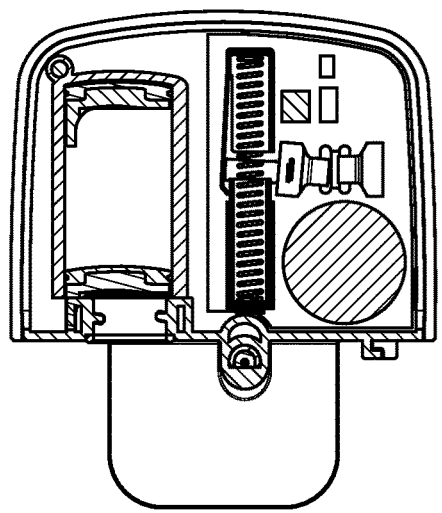

FIGS. 8A to 8O show a first embodiment of an automatic injection mechanism which in principle is constructed functionally like the preceding FIGS. 1A to 7.

In a perspective view according to FIG. 8A, the automatic insertion mechanism is shown on an infusion pump, the insertion mechanism being provided between a reservoir 11 and a pump that dispenses a substance to be dispensed into the above-described hard cannula 8 in a metered manner. In the embodiment shown, both the insertion mechanism and also the automatically detachable safety mechanism described below, as well as the pump are arranged together with the reservoir 11 on a common substrate or a common retaining surface, which can have a sticking or adhesive surface 12 on the underside, for example, in order to be adhered to a body as a so-called patch pump. The cannula 7, 8 is inserted as described by relaxing the insertion spring 4, which presses or shoots the cannulas 7, 8 in the insertion direction and ensures an ejection of the cannula 7, 8 out of the underside of the infusion pump. The cannula 7, 8 is deflected by a cannula guide 6.1 (FIG. 8D) in the desired ejection direction, which is different from the movement direction of the other insertion components. Since both soft cannula 7 and hard cannula 8 are bendable or flexible, this is not a problem. In order to prevent bending upward, a guide can be provided on the "pod roof," e.g., above the bend in the region of the cannula guide 6.1.

As is evident from FIG. 8C, the distal side of the soft cannula holder 2 shown at the left in FIG. 8C presses under the pressure of the insertion spring 4 onto the drive face or slope 1.1a, e.g., slanted region, of the triggering element 1.1 of the cannula housing 1, whereby this triggering element 1.1, which is formed as a resilient arm in a sidewall of the cannula housing 1, is subjected to a force in the release direction, as drawn in FIG. 8C by the arrow P. The triggering element 1.1 is connected via a connecting element 9.1 (FIG. 8H) to an automatically releasable safety mechanism 9 and is fixedly connected for example to a mounting 9.2a, at the end of which opposing the triggering element 1.1 a melting element 9.3 or softening element is connected, which is in turn connected at the opposite end thereof to a further mounting 9.2b, which is connected to the substrate of the patch pump, fixedly and immovably relative to the cannula housing 1 or the insertion mechanism. The melting element 9.3 thus lies between the two mountings 9.2a and 9.2b and is under tensile load from the triggering element 1.1 and thus from the insertion spring 4. If the melting element 9.3 were not present, the blocking or triggering element 1.1 could not withstand the pressure force of the soft cannula 2 caused by insertion spring 4 and the insertion movement or advancement movement of the soft cannula holder 2 would begin.

Connecting element 9.1, mountings 9.2a and 9.2b and melting element 9.3 form a fusible configuration of the safety mechanism 9.

In the vicinity of the melting element 9.3, a warming or heating element 10 is provided on the baseplate between electrical contacts which are provided, for example, in the region of milled cuts (10a and 10b); the heating element is provided on a connecting piece between the milled cuts, for example, and can be designed in the form of a heating wire or heating surface that can generate heat when electrical current flows. The electrical energy provided by the battery 13 as shown can be used for this purpose, for example.

For example, if an automatic insertion is to be triggered, current is conducted through the heating element 10 which thereby heats up, and due to this heating, softens or optionally melts the melting element 9.3 provided in the vicinity of or on the heating element 10, so that the mechanical coupling or retaining connection between the mountings 9.2a and 9.2b is interrupted or destroyed in case of a softening or weakening of the material of the melting element 9.3, for example, or a complete melting, i.e., the creation of an interruption or tear in melting element 9.3, as shown in FIGS. 8F to 8H for the sake of example. Thereby the mounting 9.2a, which is under tensile stress, is no longer held on the mounting 9.2b by the melting element 9.3 and can therefore no longer restrain the connecting element 9.1 connected to the triggering element 1.1, so that the triggering element 1.1 is pressed by the force of the insertion spring 4 out of the blocking position into the release position, as shown in FIGS. 8F to 8J. The insertion spring 4 can thus relax and trigger the insertion process as described above.

Apart from the insertion spring 4, no additional force accumulator or additional spring element is necessary for the attenuation or fusion safety according to the invention in order to implement an electrically controllable automatic insertion triggering. It is thus possible to forego additional spring elements, which enables simple and trouble-free construction of an automatic insertion mechanism.

After insertion of the soft cannula 7 has taken place, the hard cannula 8 inside the soft cannula 7 is withdrawn as described previously herein so that the extended soft cannula 7 remains in the extended state, as shown in FIGS. 8K to 8O.

Subsequently the dispensing of a substance from the reservoir 11 of the pump can begin, which dispenses the substance in a metered manner to the hard cannula 8, from which it is dispensed to the soft cannula 7 and dispensed at the distal end of the soft cannula 7 and injected, for example.

FIGS. 9A to 9O shows a second embodiment of an attenuation safety or fusion safety mechanism 9, which is in principle constructed like the embodiment according to FIGS. 8A to 8O unless otherwise described below. The reader is therefore referred to the description of FIGS. 8A to 8O, which will not be repeated.

The melting element 9.3 is again arranged between mountings 9.2a and 9.2b but, unlike the embodiment of FIGS. 8A to 8O, is formed here as a conductive plastic.

To trigger or release the insertion mechanism, a current flow through the conductive plastic or melting element 9.3 is caused, whereby the plastic is heated and sufficiently weakened that the tensile force originating from the insertion spring 4 severs the melting element 9.3, as shown in FIGS. 9F to 9J. Alternatively or additionally, the melting element 9.3 can also be separated completely by heating by means of the above-mentioned current flow.

A potential difference can be applied to the conductive plastic by the electrical contacts, thus causing a current flow through the melting element 9.3 according to Ohm's law.

Alternatively, the melting element 9.3 can also be provided with two lateral electrodes, each of which run along the longitudinal direction of the melting element 9.3, so that when a potential difference between these electrodes is applied, the electrodes separated by the melting element 9.3 cause a current flow and thus a heating of the melting element 9.3 in the form of a conductive plastic, whereby this element is weakened or severed in order to release the safety.

In the embodiment shown in FIGS. 8A to 8O and 9A to 9O, it is advantageous if the melting element 9.3 is tapered or has a relatively small cross section for example, which should be sufficiently wide or strong to provide the retaining force for the triggering element 1.1 for retaining the safety. A tapering or reduction of the cross section of the melting element 9.3 allows an easy melting or opening of the safety.

Figure 10A:
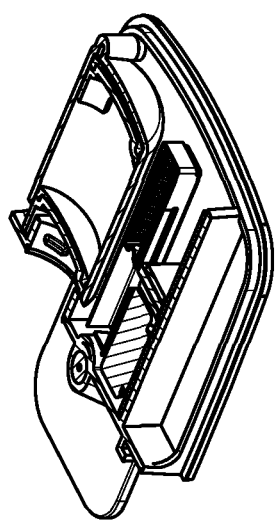
Figure 10B:
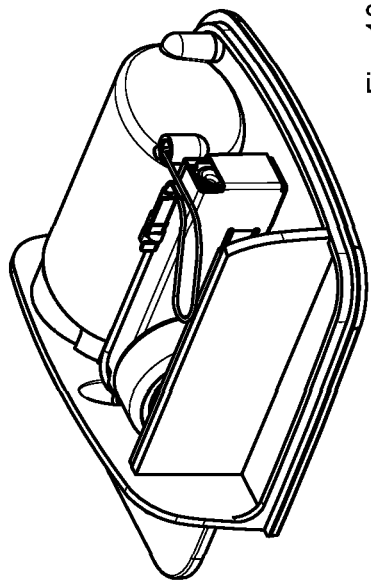
Figure 10E:
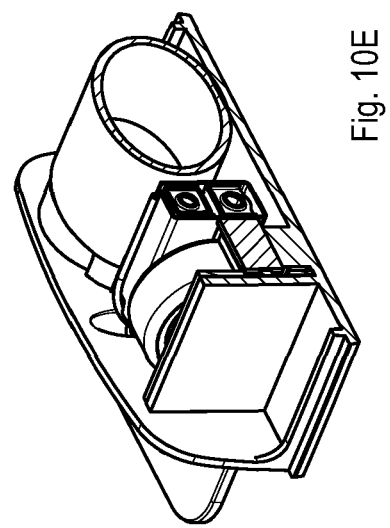
Figure 10D:
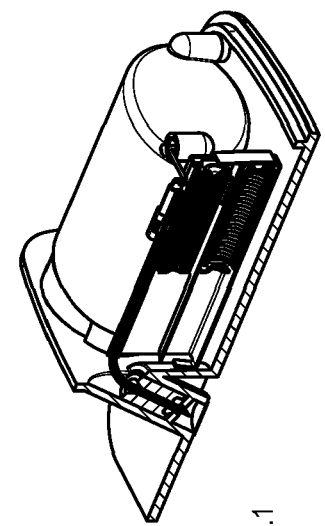

FIGS. 10A to 10A show a third embodiment, which is in principle identical to the previously described embodiments unless otherwise described.

The triggering element 1.1 of the cannula housing 1 is pressed by the insertion spring 4 in the lateral direction due to the drive face or slope 1.1a, i.e. orthogonally to the longitudinal direction of the insertion spring 4. A softening element or melting element 9.4 prevents the triggering element 1.1 from being able to move out of the blocking position into the release position. The melting element 9.4 can be formed in a rod shape or as an elongated body, for example. The melting element 9.4 can consist of a softenable or fusible material.

Figure 10C:
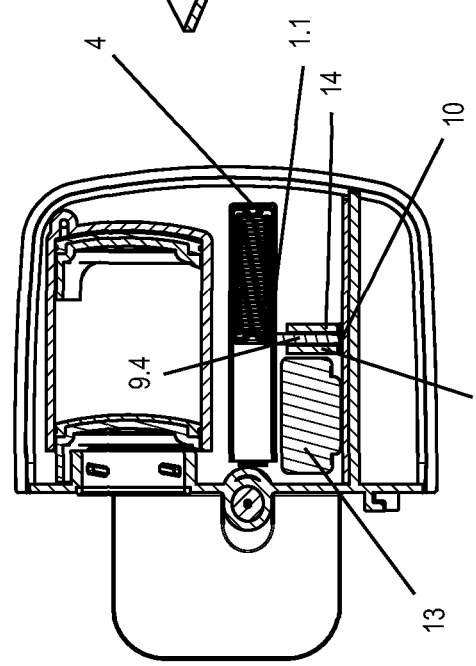

In the vicinity of the melting element 9.4, a warming or heating element 10 is provided which can heat or at least partially melt the melting element 9.4 in order to weaken or destroy the retention force thereof against the force of the triggering element 1.1 that is pressing toward the released position. In the embodiment shown in FIG. 10C for example, the heating element 10 can be provided in the region of melting element 9.4 that is opposite the region with which the triggering element 1.1 is in contact. It is also possible to provide the heating element 10 at a different point, for example in the region of the contact with triggering element 1.1 or in the region of the guide elements 14 which enable a displacement of the melting element 9.4 in the axial direction.

If the heating element 10 is heated, for example by being formed as an electrical heating element through which current flows, then the melting element 9.4 softens or melts and can no longer withstand the pressure exerted by the triggering element 1.1, so that the melting element 9.4 is shortened, for example, due to a partial melting process, whereby the triggering element 1.1 is pressed out of the blocking position into a release position, as shown in FIG. 10H for the sake of example. Thereby the insertion can be triggered.

A melting element in all embodiments can include or consist of a thermoplastic material for example, such as a copolymer, and upon heating can be melted partially or completely, wherein the fluid phase of the material can also serve as a sliding or lubricant agent so that an optionally remaining solid part of the melting element can move more easily within an optionally provided guide, for example.

FIGS. 11A to 11O show a fourth embodiment, which is constructed similarly to the third embodiment.

In place of the melting element 9.4 of the third embodiment, a tappet 15 is provided, which can be designed to be softenable or fusible or alternatively can be constructed of a non-melting or non-softening element. The tappet 15 is in turn guided displaceably axially in guide elements 14 and holds the blocking or triggering element 1.1 pressing on the tappet 15 in the blocking position. At the side of the tappet 15 opposite the blocking or triggering element 1.1, the tappet 15 is supported on a softenable or fusible retaining plate or element 9.5, which is formed from a fusible or softenable plastic, for example, or from a conductive plastic or metal. If the retaining element 9.5 is heated by a heating element for example, or if a current flows through it if it is designed to be conductive, the retaining element 9.5, which is provided to be fixed and immovable relative to the cannula housing 1 in the initial position, heats up and loses the ability to support the tappet 15 against the pressure force acting on the blocking or triggering element 1.1. FIG. 11H shows the state after triggering, i.e. partial melting or softening of the retaining element 9.5, whereby the blocking or triggering element 1.1 can move out of the blocking position into the release position, e.g., triggered, and a subsequent insertion can take place.

According to one embodiment, the retaining element 9.5 can be a solid element that is fastened by a solder or adhesive bond to a housing, of the infusion device for example. This fastening can be released by heating.

Figure 12B:
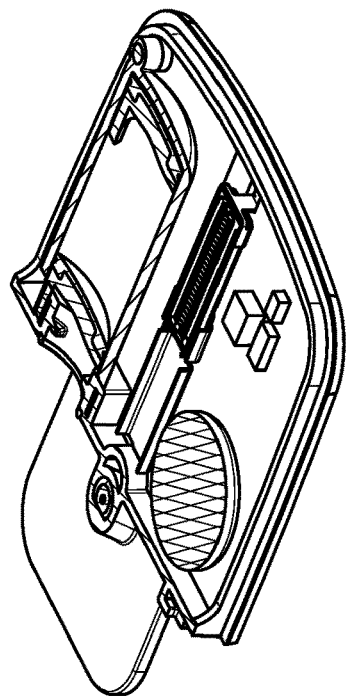
Figure 12E:
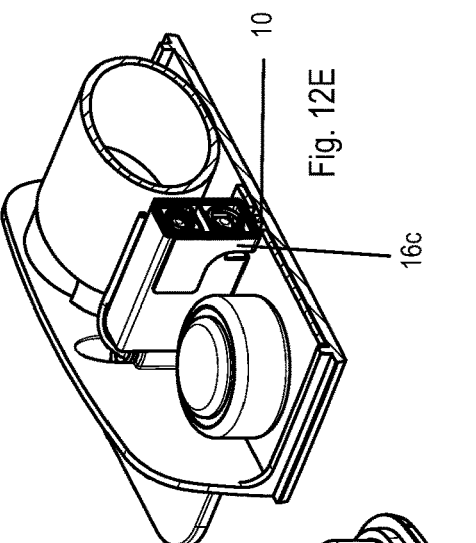
Figure 12D:
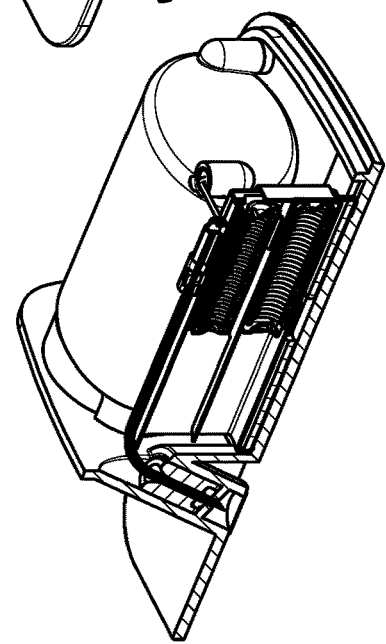
Figure 12A:
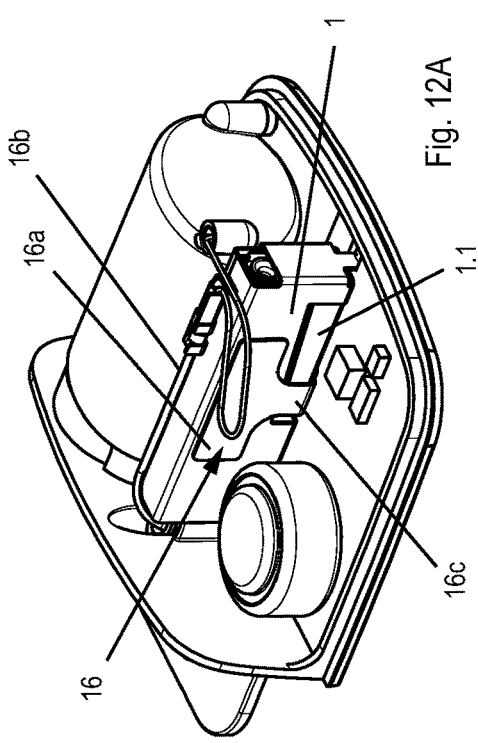
Figure 12C:
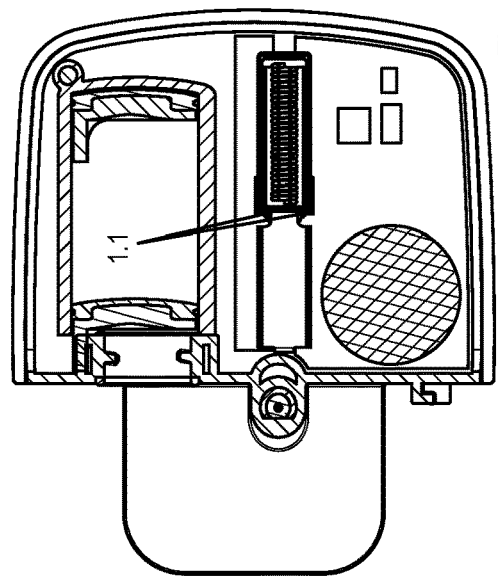

FIGS. 12A to 12O show a fifth embodiment, wherein a film 16 or a sheet-like element is provided on the triggering element or elements 1.1 in order to hold the triggering elements 1.1 in a blocking position in the initial state. The film 16 can be adhered or tensioned across the triggering elements 1.1. For example, the film 16 can be glued to a housing side of the cannula housing 1 or fastened thereon in some other manner, for example welded or clamped, and due to the application or mounting of the film 16 on the cannula housing 1, preferably at multiple points of the film 16, the film 16 can hold the blocking or triggering element 1.1 or elements in the blocking position.

In the embodiment shown in FIGS. 12A to 12O, the film can be formed as a double-T structure for example, wherein two broadened gluing regions or application regions 16a and 16b are provided at opposite ends of the film 16 and are connected by a narrower or tapered film center application region 16c. The film 16 can be attached or melted or glued with the broad application regions 16a and 16a on opposing side faces of the cannula housing 1 for example, so that the narrow connecting or application region 16c extends across the triggering element or elements 1.1 and holds them in the blocking position, as shown in FIG. 12A.

A heating element 10 can be provided on or in the vicinity of the film 16, for example on or in the region of the narrower film of the application region 16c, and can be used for heating the film 16. The film 16 can consist of a plastic, for example, or some other material whose mechanical retaining or supporting capability can be weakened by heating, so that after heating of the film 16 by the heating element 10, the film 16 either softens or widens or optionally also tears, whereby the retaining force of the film 16 for holding the triggering element 1.1 pressing out of the blocking position into the release position is weakened and therefore, as shown in FIGS. 12F, 12H and 12J, the film 16 can no longer hold the retaining elements provided by the blocking or triggering element 1.1 in the blocking position, so that they reach the release position and the insertion is triggered.

Figure 13B:
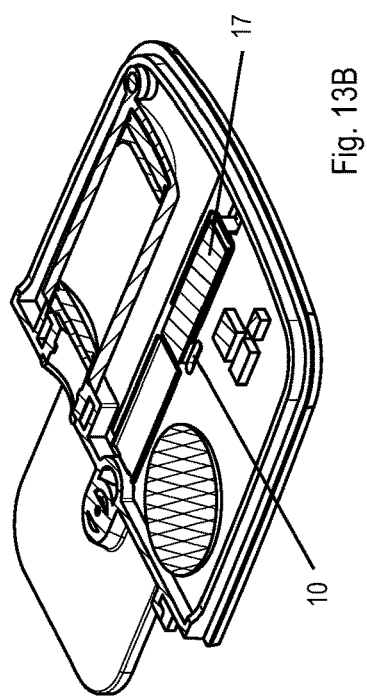
Figure 13A:
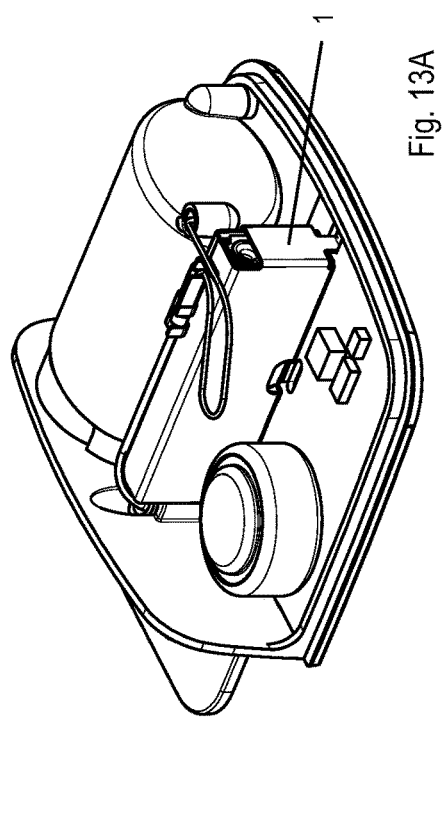
FIGS. 13A to 13O show a sixth embodiment of an automatically releasable safety mechanism.
Figure 13E:
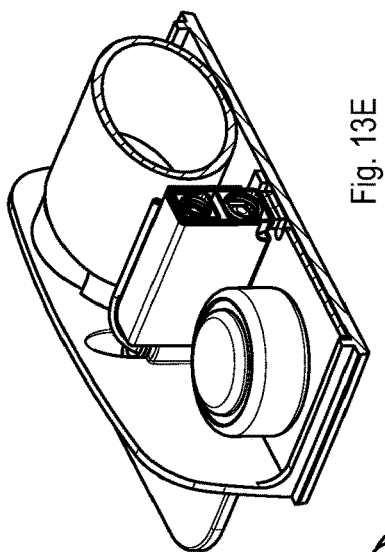
Figure 13D:
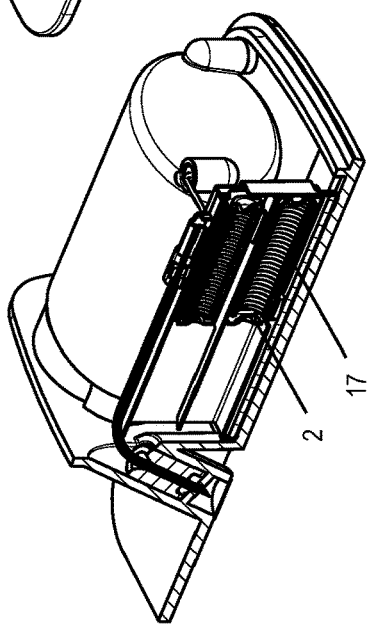
Figure 13C:
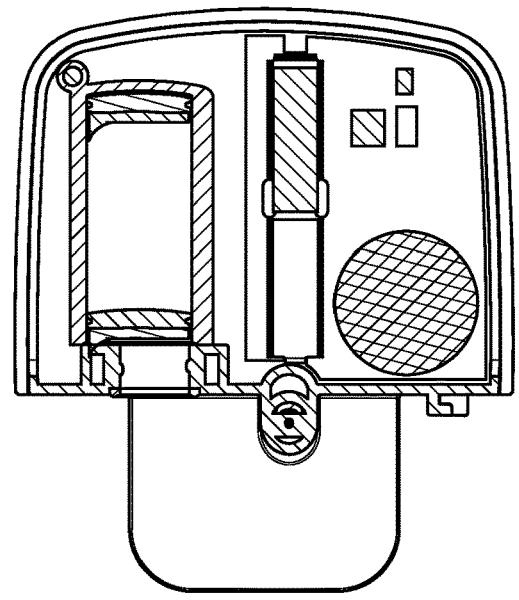
Figure 13O:
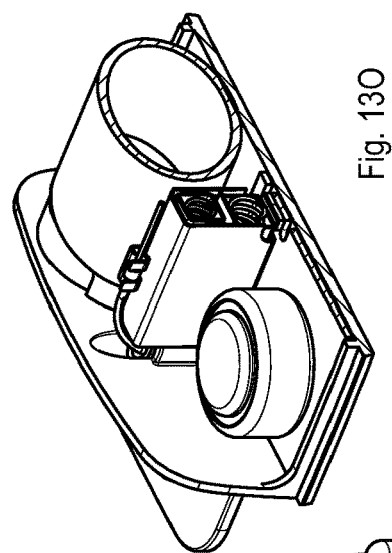
Figure 13L:
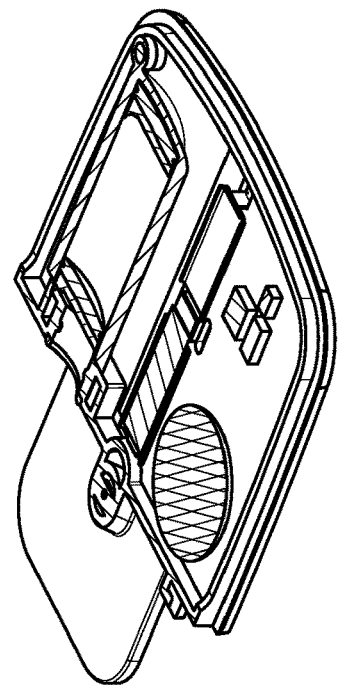
Figure 13N:
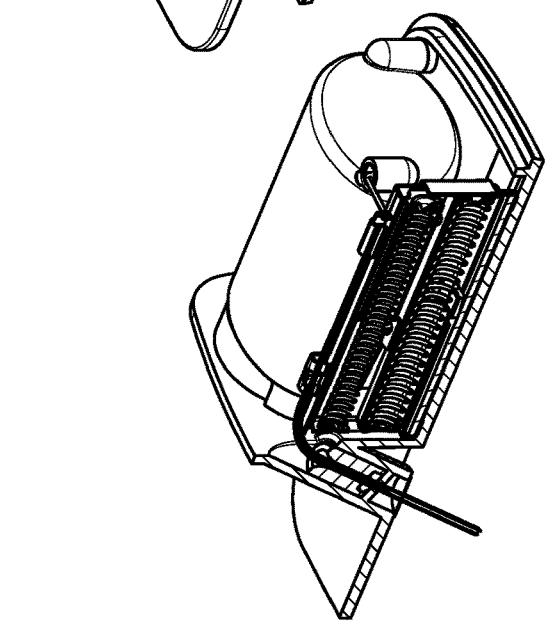
Figure 13K:
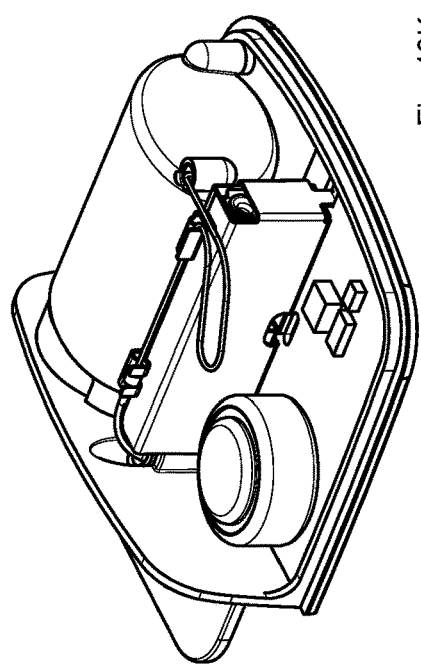
Figure 13M:
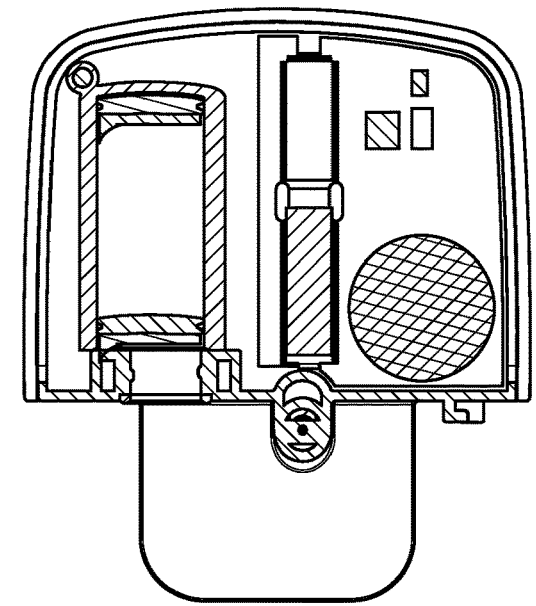

FIGS. 13A to 13O show a sixth embodiment of an automatically releasable safety, wherein, unlike the preceding embodiments, no triggering elements 1.1 are provided. Instead, the soft cannula holder 2 is held in position, immovable relative to the cannula housing 1 against the force of the insertion spring 4 in that the soft cannula holder 2 is glued relatively immovably onto the cannula housing 1. The holding or adhesive surface 17 for holding the soft cannula holder 2 can be provided on the cannula housing 1, for example, or alternatively or additionally on the substrate of the patch pump.

The adhesive surface 17 is implemented by means of an adhesive material that loses its adhesive force or holding force when heated, so that the adhesive material can be softened by means of a warming or heating element 10, an electrical heating element 10 for example, which is provided on or in the vicinity of the holding or adhesive surface 17. In this way, the stationary retention of the soft cannula holder 2 can be weakened or canceled until the pressure force acting on the soft cannula holder 2 due to the insertion spring 4 is greater than the holding force of the holding or adhesive surface 17, so that the soft cannula holder 2 can move relative to the housing by the driving of the insertion spring 4, whereby an insertion is triggered as shown in FIGS. 13F to 13J.

Safety and triggering mechanisms which can be used for an insertion mechanism as described in the embodiments according to FIGS. 1 to 7, for example, will be described below.

FIG. 14 shows an embodiment having a fusible medium 9.6 loaded under pressure, which can be arranged between the heating element 10 and the triggering element 1.1, for example, as described above. The triggering element 1.1 can be subjected to a constant stress which is caused by the insertion spring 4, as shown symbolically by the arrow. In the embodiment shown, the fusible medium 9.6, which is present in a solid state, surrounds the heating element 10 at least on the upper side. and on the lateral faces as well in the embodiment shown, wherein the heating element 10 is arranged on a substrate or base element 18.

In this embodiment, the fusible material or fusible medium 9.6 could be a hot-melt glue. A tolerance is compensated automatically.

If the heating element 10 is heated, the fusible medium 9.6, such as a hot melt glue, is heated or softened, whereby the triggering element 1.1 loaded by the constant stress (indicated by the arrow in FIG. 14) can press the softenable or fusible medium 9.6 in the direction toward the heating element 10 and thus cancel a blocking state for example, so that an insertion as described above can be released or triggered.

FIG. 15 shows an additional embodiment similar to the embodiment described in FIG. 14, wherein the fusible medium 9.6 is provided on the heating element 10, but does not surround or cover it on the side faces. For example, the fusible medium 9.6 could be tin solder or hot-melt glue and could also have an adhesive property in order to hold the triggering element 1.1 in the triggered state, for example.

The triggering takes place as described above by heating of the heating element 10 and softening or melting of the softenable or fusible medium 9.6, whereby the triggering element 1.1 can be pressed or pushed by the constant stress originating from the insertion spring 4 or some other mechanism out of the safety position shown in FIG. 15 in the direction toward the heating element 10 in order to cancel a blocking position.

FIG. 16 shows an embodiment in which a force or constant stress (indicated by the arrow) acts on the triggering element 1.1 or a tappet which is arranged completely or at least partially in a guide elements 14, e.g., a hollow cylinder, on one side of a softenable or fusible medium 9.6, which is surrounded by the guide elements 14 or the hollow cylinder and contacts a heating element 10 on the side opposite the triggering element 1.1. An outflow opening 14a, which is formed between the triggering element 1.1 and the guide elements 14 or the hollow cylinder, is provided on the lateral edge of the triggering element 1.1.

If the heating element 10 is heated, then the fusible medium 9.6 can melt and escape through the outflow opening 14a if it is subjected to pressure caused by the constant stress acting on the triggering element 1.1, whereby the triggering element 1.1 is moved in the direction toward the heating element 10 from a blocking position into a release position.

The heating energy required in this embodiment is greater compared to the two previously described variants because more material has to be heated up. Softer materials can be used for the fusible medium 9.6 because it is enclosed by the guide elements 14 or the hollow cylinder. The fusible medium 9.6 may be a non-adhesive material and is a slowly cooling material, for example, so that this material does not become rigid before it can flow away through the outflow opening 14a.

FIG. 17 shows another embodiment, which is constructed similarly to FIG. 16, wherein the outflow opening 14b is not formed by a gap between the tappet or triggering element 1.1 and the guide elements 14, but rather is provided directly in the guide elements 14, e.g. at a height of the guide elements 14 at which the heating element 10 adjoins the fusible medium 9.6.

FIG. 18 shows another embodiment, in which the force on the blocking element can be reduced or stepped down by deflection. An element marked 2, such as a soft cannula holder, can be subjected to a constant load or a force from the direction marked by the arrow, which force contacts a drive face or slope 1.1a of a triggering element 1.1 and applies a pressure acting transversely or perpendicular to the force acting as a constant stress. The triggering element 1.1 contains a structure to be melted or a fusible medium 9.6 which contacts a heating element 10. If the heating element 10 is heated up, then the softenable or fusible medium 9.6 is softened or melted, whereby the triggering element 1.1 is moved by the force acting on element 2 from a blocking position into a release position and can release or trigger an injection process.

FIG. 19 shows an embodiment in which an element marked 2, such as a soft cannula holder, is subjected to a force by an insertion spring and acts on a triggering element 1.1 due to the drive face or slope 1.1a as shown and applies a force to the triggering element in the lateral direction, or release direction. The triggering element 1.1 has a fusible medium 9.6 which can be subjected both to a compressive force and a shearing force in the embodiment shown. If the fusible medium 9.6 is softened or melted, e.g. by heating of the heating element 10, the triggering element 1.1 can be pressed out of the blocking position drawn in FIG. 19 into a release position transversely or perpendicularly to the force acting as a permanent stress and can thus release or trigger an insertion.

FIG. 20 shows an embodiment similar to the embodiment shown in FIGS. 13A to 13O, in which a holding surface or an adhesive surface 17 is provided on a heating element 10 and, unlike the embodiment according to FIGS. 13A to 13O, does not directly contact an element to be held such as a soft cannula holder 2, but instead holds a blocking element adhered thereto, directly or by means of a structure 19, in a blocking position. The blocking element structure 19 is subjected to a force by the element to be retained or the soft cannula holder 2 and in turn presses onto the structure held by the holding surface or adhesive surface 17. If the holding surface or adhesive surface 17 is weakened or melted by the heating element 10, then the structure connected thereto can be pressed away by the blocking element, in which case a shearing stress and a compressive stress act on the adhesive point. The blocking element can thus be pushed into the release position by the element 2 to be retained, which can trigger an insertion.

FIG. 21 shows an embodiment in which blocking and heating elements are combined. This can allow heating or heat to act directly, which can increase the efficiency.

A triggering element 1.1, such as the above-described blocking or retaining element or triggering element inserter, is under constant stress as indicated by the arrow and in turn presses on an electrically conductive softenable or fusible medium 9.6 which is provided between two electrical contacts 10c. If a voltage is applied between the electrical contacts 10c, then a current flows through the fusible electrically conductive softenable or fusible medium 9.6, which leads to a heating of the fusible medium 9.6 and a softening or melting or weakening of the medium 9.6, so that the triggering element 1.1 can be pressed in the direction of the medium 9.6 or in the direction toward the electrical contacts 10c, from a blocking position into a release position.

FIG. 22 shows an embodiment in which a triggering element 1.1 presses onto an electrically conductive fusible medium 9.6 which is provided between electrical contacts 10c. The fusible medium 9.6 can be a conductive plastic such as PreElec®-PP1380 manufactured by Premix Thermoplastics, which is a conductive polypropylene, and in order to release the triggering element 1.1, an electrical voltage is applied between the electrical contacts 10c, whereby a current flows in the fusible medium 9.6 and softens it.

FIG. 23 shows an embodiment in which an element 2, such as a soft cannula holder, is subjected to pressure and held by a fusible medium 9.6 which can be weakened or softened or melted by a heating element 10. The fusible medium 9.6 here is under tensile stress in the heating region or in the vicinity of the heating element 10, so that relatively little material or volume of the fusible medium 9.6 need be heated, because the stress in the medium or fusible material 9.6 becomes greater and greater the smaller the cross section becomes.

FIG. 24 shows an embodiment in which a fusible or softenable or weakenable fusible medium 9.6 is provided similarly to a designed breaking point on one or more triggering elements 1.1 and holds it or them in a blocking position. A heating element 10 inside the fusible medium 9.6 is provided in the embodiment shown. A constant stress from the element 2 such as a soft cannula holder, which presses on the triggering element or elements 1.1, acts on each of the triggering elements 1.1, which are held in the blocking position by the fusible medium 9.6. If the heating element 10 is heated up, then the fusible medium 9.6 is softened or weakened or melted so that the triggering elements 1.1 can no longer hold the element 2, whereby an insertion can be released or triggered.

Figure 25B:
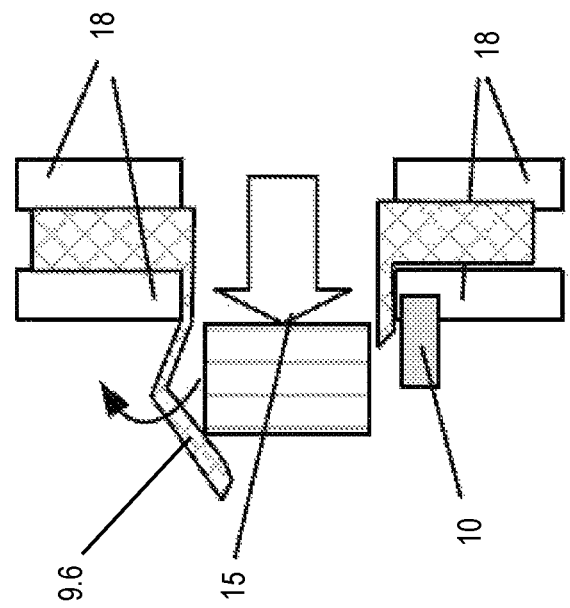
Figure 25A:
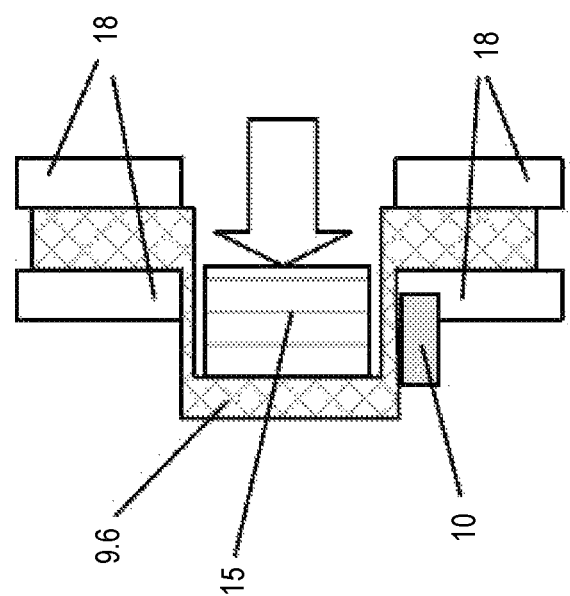

FIG. 25A shows an embodiment similar to the embodiment described in FIGS. 11A to 11O. A force is applied to a softenable or weakenable fusible medium 9.6 by a tappet 15, which holds a soft cannula holder 2 in the blocking position as shown in FIG. 11C, and presses on the fusible medium 9.6 as shown in FIG. 25A.

If the fusible medium 9.6 is weakened or softened or melted by heating of the heating element 10, the element can no longer withstand the stress from the tappet 15, whereby the tappet 15 is displaced and can release an insertion, as shown in FIG. 25B. The retaining force for the fusible medium 9.6 is distributed onto two connecting pieces. Only one of these two connecting pieces is softened, which can reduce the heating region and thus increase efficiency.

Figure 26:
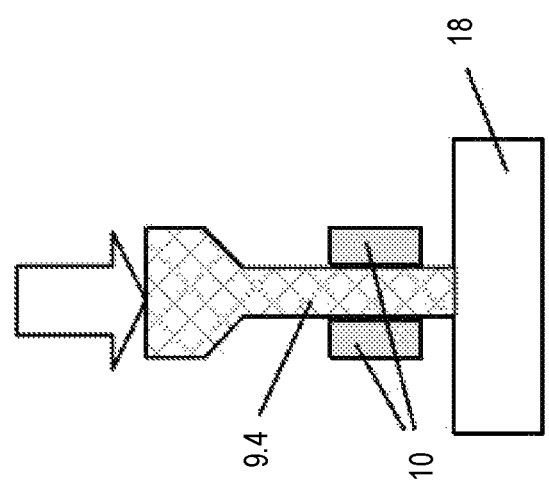

FIG. 26 shows an embodiment similar to the embodiment shown in FIGS. 10A to 10O, in which a melting element 9.4 (e.g., fusible element) is under compressive stress and—unlike that shown for the embodiment of FIGS. 10A to 10O—is heated by lateral heating elements 10 which can be provided in the region of the guide elements 14 shown in the embodiment of FIGS. 10A to 10O. If the fusible material of the melting element 9.4 is heated by the heating element or elements 10, the softened or melted material alongside the heating element or elements 10, e.g. in the intermediate space between heating element 10 and base element 18, can escape. In the embodiment shown, a heating element 10 is only under relatively low mechanical stress.

Figure 27:
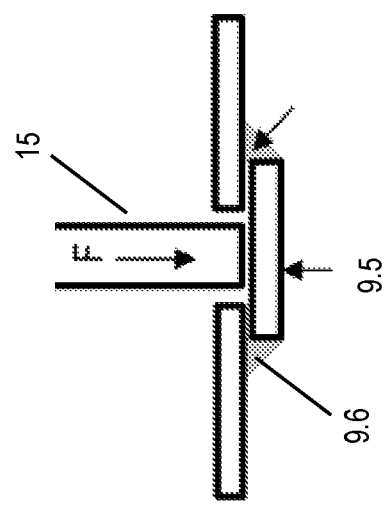
FIGS. 26 and 27 show embodiments in which a safety element is soldered off.

FIG. 27 shows an embodiment similar to or like FIGS. 11A to 11O.

In general, it can be advantageous if a direct contact is present between a warming or heating element 10 and the fusible medium 9.6 of the safety element or mechanism 9, as shown for example in the above-described variants in which the fusible medium 9.6 is under compressive or shearing stress. A material that can be softened and/or melted by the supply of heat, for example, is used as the fusible medium 9.6. As mentioned several times above, a material can also be used which itself serves as an electrical conductor or has electrically conductive properties and thus can be heated and weakened or melted on its own by means of current flow.

A fusible trigger made from plastic should meet the following requirements, for example: The fusible safety serves as a retaining element for the triggering mechanism for several years. A creep-resistant plastic that is also not prone to stress cracks should therefore be considered. Because the plastic material must not stretch or tear during storage, care must be taken that the yield stress is greater than 45 MPa and the elongation at yield is less than 5%.

The softening temperatures, e.g. Vicat and HDT temperatures, should be in the range of 85° C. to 115° C. The different softening temperatures should also be close to one another and the plastic should be amorphous and have a low heat capacity, e.g. under 2400 J/kg.

Plastics—Background Information

The characteristics of the temperature profiles for semi-crystalline and amorphous plastics differ as follows:

During melting of a crystalline solid body, heat must be supplied at the melting point (latent heat of fusion) in order to break up the crystalline structure; the temperature cannot be increased during this process. For an amorphous solid body, however, all the supplied energy is used for increasing the temperature of the material.

Semi-Crystalline Plastics

The solid body must first be heated to the melting temperature; thereafter the heat of fusion must be added in order to transition to a melt. Under constant pressure and without taking into consideration losses (e.g. from conduction, radiation or convection), the following holds:

$$Q_{melt} = c \cdot m \cdot (T_m - T_a) + H_{fus} [J]$$

Amorphous Plastics

For amorphous plastics, only the heat capacity until the glass-transition temperature is reached is considered. Under constant pressure and without taking into consideration losses (e.g. from conduction, radiation or convection), the following holds:

$$Q_{melt} = c \cdot m \cdot (T_g - T_a) [J]$$

Q heat quantity
m mass of the plastic to be melted [kg]
c specific heat capacity [J/(kg–K)]
$H_{fus}$ heat of fusion [J]
$T_m$ melting temperature [° C.]
$T_g$ glass transition temperature [° C.]
$T_a$ ambient temperature [° C.]
$H_{fus}$ [J]: Heat of fusion refers to the quantity of energy that is required in order to cause a substance sample at its melting point to melt, under constant pressure (isobar), i.e. to transition from the solid to the fluid aggregate state.
c [J/(kg–K)] The specific heat capacity is a thermodynamic material property. It measures the capability of a substance to store thermal energy.

Determining the Power Required to Melt a Plastic

The power can be determined as a function of the time that is used to supply the quantity of heat for melting.

$$P_{melt} = \frac{Q_{melt}}{t} \left[ W = \frac{J}{s} \right]$$

Table 1 in FIG. 28 shows for the sake of example a selection of plastics and the corresponding period to melt or soften a defined volume of plastic (without taking losses into consideration). The final line lists the duration of energy supply until the plastic has softened. The results show that semi-crystalline plastics demand markedly more time and, above all, a higher temperature for melting as well.

Information from Plastics Datasheets

A variety of information regarding thermal properties can be found in plastics datasheets. Usually either the HDT—heat deflection temperature—or the Vicat softening temperature is indicated. The HDT temperatures are determined according to DIN EN ISO Standard 75-1, -2, and -3 (predecessor: DIN 53461). There is a distinction in the standard between variants A, B and C. The Vicat softening is determined according to DIN EN ISO Standard 306 (predecessor: DIN 53460).

Suitable Plastics

Table 2 in FIG. 29 shows a selection of plastics. The selection is not exhaustive. The points mentioned above are considered for the selection.

Under the precondition that the given heating element reaches a temperature in the range of 120±5° C., plastics having a Vicat temperature of 85-115° C. are suitable for melting. If the heating element can produce a higher heating power, then additional plastics can be considered.

Reinforced plastics are particularly suitable. As well as those for which the difference between HDT A and HDT B is small.

Dimensioning

Components made from plastic are dimensioned according to the following literature:

Gottfried W. Ehrenstein; Mit Kunststoffen konstruieren (ISBN 978-3-446-41322-1)

Gunter Erhard; Konstruieren mit Kunststoffen (ISBN 3-446-22589-7)

The permissible stress of the structure to be loaded is determined as follows:

$$\sigma_{zul} = \frac{K}{S \cdot A}$$

$\sigma_{zul}$=permissible tension
K=short-term strength characteristic
S=safety factor
A=material reduction factor (product of the below mentioned material reduction single factors)
Material reduction single factors $A_T$ Strength loss due to temperature influence rel. to 20°
$A_{st}$ Strength loss due to idle time stress
$A_{dyn}$ Strength loss due to dynamic stress
$A_A$ Influence of aging
$A_W$ Influence of water (considerable for PA)
$A_K$ Notch influence
$A_{BN}$ Weld line
$A_F$ Production influence (1.05-1.25)
$A_{ex}$ Uncertainty in determination of characteristic values (extrapolation or inaccurate knowledge of stress)

Calculation example for determining reduction and safety factors for an amorphous thermoplastic on the example of an ABS (acrylonitrile-butadiene-styrene copolymer):

The following Table 3 shows the material reduction individual factors on the example of an ABS (acrylonitrile-butadiene-styrene copolymer):

TABLE 3

| Mechanical Prroperties | ABS | ABS |
|---|---|---|
| Short-term strength characteristic K (N/mm2 = MPa) | 45 | 45 |
| Safety factor S | 2 | 2 |
| Reduction factors (Ehrenstein p. 91) A | 2.622 | 5.182 |
| Reduction factors (Ehrenstein p. 91) A including safety factor | 5.244 | 10.364 |

TABLE 3-continued

|  | ABS | ABS |
|---|---|---|
| Permissible tension [N/mm2] | 8.581 | 4.342 |
| Required minimum cross-sectional area [mm2]_max force | 0.655 | 1.294 |
| Force | 0.349 | 0.691 |
| Required minimum cross-sectional area [mm2]_max force | 0.139 | 0.275 |
| Edge length, square cross section [mm] | 0.81 | 1.14 |
| Diameter of circular cross section [mm] | 0.91 | 1.28 |
| Holding the spring force (direct) | | |
| Required minimum cross-sectional area [mm2] | 1.17 | 2.30 |
| Derivation of the reduction factor | | |
| $A_T$ Strength loss due to temperature influence rel. to 20° | 1.036 | 2.410 |
| Temperature | 23 | 70 |
| k | 0.0117 | 0.0117 |
| $A_{st}$ Strength loss due to idle time stress | 2 | 1.7 |
| Duration of stress | Years | 4 days |
| $A_{dyn}$ Strength loss due to dynamic stress | 1 | 1 |
| $A_A$ Influence of aging | 1 | 1 |
| $A_W$ Influence of water (considerable for PA) | 1 | 1 |

TABLE 3-continued

|  | ABS | ABS |
|---|---|---|
| $A_K$ Notch influence | 1 | 1 |
| $A_{BN}$ Weld line | 1 | 1 |
| $A_F$ Production influence (1.05-1.25) | 1.15 | 1.15 |
| (knowledge of stress) | 1.1 | 1.1 |

A stress on ABS for 96 h at 70° C., for example, results in a higher reduction factor, including safety factors of 10.4, than the stress at 23° C. over several years (reduction factor including safety factors of 5.2).

If one therefore considers a reduction of the permissible tension by the reduction factor including safety factors of 10.4, a value of 4.3 MPa results for the permissible stress for mechanical loading of an ABS component.

Isochronous stress-strain diagrams or value tables can be used to estimate the total deformation or strain of a structure of a plastic component at a given load for a given stress duration and ambient temperature. The values are based on tensile tests.

The following Table 4 has stress-strain characteristics of an ABS plastic at 23° C. for different stressing times:

TABLE 4

Stress-strain (isochronous) 23° C. Teluran ® GP-22, ABS, INEOS Styrolulion

| 10 h | | 100 h | | 1000 h | | 10000 h | | 100000 h | |
|---|---|---|---|---|---|---|---|---|---|
| Strain in % | Stress in MPa | Strain in % | Stress in MPa | Strain in % | Stress in MPa | Strain in % | Stress in MPa | Strain in % | Stress in MPa |
| 0 | 0 | 0 | 0 | 0 | 0 | 0 | 0 | 0 | 0 |
| 0.1464 | 3 | 0.1608 | 3 | 0.1895 | 3 | 0.2472 | 3 | 0.3629 | 3 |
| 0.23 | 4.7 | 0.2534 | 4.7 | 0.3009 | 4.7 | 0.3971 | 4.7 | 0.5918 | 4.7 |
| 0.3142 | 6.4 | 0.3479 | 6.4 | 0.4166 | 6.4 | 0.5572 | 6.4 | 0.8443 | 6.4 |
| 0.3995 | 8.1 | 0.4448 | 8.1 | 0.5382 | 8.1 | 0.731 | 8.1 | 1.1284 | 8.1 |
| 0.4862 | 9.8 | 0.5452 | 9.8 | 0.668 | 9.8 | 0.9236 | 9.8 | 1.4556 | 9.8 |
| 0.5751 | 11.5 | 0.6505 | 11.5 | 0.809 | 11.5 | 1.142 | 11.5 | 1.8416 | 11.5 |
| 0.6669 | 13.2 | 0.7625 | 13.2 | 0.9654 | 13.2 | 1.3957 | 13.2 | 2.3082 | 13.2 |
| 0.7625 | 14.9 | 0.8836 | 14.9 | 1.1428 | 14.9 | 1.6975 | 14.9 | 2.8848 | 14.9 |
| 0.8634 | 16.6 | 1.0168 | 16.6 | 1.3481 | 16.6 | 2.064 | 16.6 | 3.6105 | 16.6 |
| 0.9516 | 18 | 1.1382 | 18 | 1.5447 | 18 | 2.4295 | 18 | 4.3558 | 18 |

Quelle: https//www.campusplastics.com/campus/en/datasheet/Teduran%C2%AE+GP-22/INEOS+Styrolution/654/78717c93/S1?pos=0

The following Table 5 has stress-strain characteristics of an ABS plastic at 60° C. for different stressing times:

TABLE 5

Stress-strain (isochronous) 60° C., Terluan ® GP-22, ABS, INEOS Styrolution

| 10 h | | 100 h | | 1000 h | | 10000 h | | 100000 h | |
|---|---|---|---|---|---|---|---|---|---|
| Strain in % | Stress in MPa | Strain in % | Stress in MPa | Strain in % | Stress in MPa | Strain in % | Stress in MPa | Strain in % | Stress in MPa |
| 0 | 0 | 0 | 0 | 0 | 0 | 0 | 0 | 0 | 0 |
| 0.1132 | 1.5 | 0.1559 | 1.5 | 0.2393 | 1.5 | 0.4022 | 1.5 | 0.7205 | 1.5 |
| 0.2058 | 2.7 | 0.2855 | 2.7 | 0.4419 | 2.7 | 0.7492 | 2.7 | 1.353 | 2.7 |
| 0.3016 | 3.9 | 0.4222 | 3.9 | 0.6604 | 3.9 | 1.1309 | 3.9 | 2.0604 | 3.9 |
| 0.4023 | 5.1 | 0.5695 | 5.1 | 0.9016 | 5.1 | 1.5613 | 5.1 | 2.8719 | 5.1 |
| 0.5098 | 6.3 | 0.7314 | 6.3 | 1.1741 | 6.3 | 2.0585 | 6.3 | 3.8253 | 6.3 |
| 0.6266 | 7.5 | 0.9132 | 7.5 | 1.489 | 7.5 | 2.6457 | 7.5 | 4.9693 | 7.5 |
| 0.7558 | 8.7 | 1.1214 | 8.7 | 1.8602 | 8.7 | 3.3524 | 8.7 | 6.3669 | 8.7 |
| 0.9011 | 9.9 | 1.3643 | 9.9 | 2.3051 | 9.9 | 4.2162 | 9.9 | 8.0984 | 9.9 |
| 1.0674 | 11.1 | 1.6518 | 11.1 | 2.8457 | 11.1 | 5.2843 | 11.1 | 10.2657 | 11.1 |
| 1.2953 | 12.5 | 2.0604 | 12.5 | 3.6335 | 12.5 | 6.8677 | 12.5 | 13.5171 | 12.5 |

Quelle: https://www.campusplastics.com/campusierildatasheet/Teduran%C2%AE+GP-22/INEOS+Styrolution/654/78717c93/S1?pos=0

The example of the ABS dimensioning yielded a permissible tension of 4.3 MPa for the stressing over 96 h at 70°.

From the isochronous stress-strain value tables it is possible to estimate how high the overall deformation of the component structure is if the load is applied for a defined time and a defined temperature:

Example

Load case 1: 4.3 MPa at 23° C. over 100,000 h (~11.4 years)→strain of ~0.5%
Load case 2: 4.3 MPa at 70° C. over 100 h→strain of ~0.55%

Electrically Conductive Plastic

Electrically conductive plastic is electrically conductive and preferably a thermoplastic. It is frequently used in ESD-critical areas (e.g. packaging).

There is a distinction for electrically conductive polymers between intrinsically conductive polymers and those that become conductive due to fillers.

The material can be fine-grained carbon black or aluminum flakes, for example. Due to the size of the filler particles—conductive carbon black particles can be in the nanometer range—the filler is homogeneously distributed in the entire component. The conductivity of the plastic is therefore not dependent on whether a piece is contacted on the edge or in the center. That also makes it possible to form even very small parts or geometries that act as a melting point without receiving edge influences.

The more intimate the connection between the plastic component and the electrodes, the lower the transition resistance becomes. The largest possible contact area is optimal. A small transition resistance is obtained by connecting the electrodes to the plastic by gluing, welding or threaded fastening. The material and surface properties of the electrodes also play an important part for the transition resistance.

Findings from Measurements

An element made from electrically conductive plastic can be dimensioned to a desired electrical value:

$$R = R_\square * \frac{L}{B}$$

R: resistance value of the element [ohm]
$R_\square$: specific resistance [ohm·cm]
L: distance between the electrodes [m]
B: width of the element [m]

The electrically conductive material Pre-Elec® PP1380 has a specific resistance of 5 ohm·cm at 25° C. This value changes under the influence of temperature. At a temperature of 80° C., it is three times the value at 25° C. At a temperature of 140° C., it again has the same value as at 25° C.°.

Ignoring the temperature, the resistance value changes very little. Even if a material is punctured by an object, the conductivity remains largely preserved. A welded contact remains stable and is still intact after cooling.

One of the advantages of the electrically conductive plastic is that a component simultaneously functions as a heater and as an element to be melted. It enables a compact structure, and additionally, losses from heat radiation and heat transition are reduced. The electrically conductive plastic additionally offers a high level of design freedom for the geometry and can be efficiently produced by injection molding.

Heating Wire

Idea: The element to be melted is surrounded by a metallic coil. Due to the high conductivity of the metal, a wire becomes long if it is to achieve a desired electrical resistance value. The following materials, among others, are fundamentally suitable for such an application: aluminum, zinc, tin, copper and tungsten.

The advantages of this variant are that the wire material is easily available and comparatively inexpensive. Moreover, the area to be softened can be directly wound by the wire, or the wire can be directly embedded during injection molding. Thereby the distance between the heat source and the cross section to be heated is very small and tolerances can be canceled.

The specific resistance of the material should be sufficiently large that a suitable length of the wire results. The length of the wire should be on the order of 10 mm. For operation with a battery, the resistance value should be between 10 and 20 ohms. A practical amount of heat power to heat the wire to the desired temperature can be achieved with these values. Specific resistance values for suitable materials are in Table 6:

TABLE 6

| Material | Spec, resistance ρ 20° C. (ohm*mm2/m) |
| --- | --- |
| Aluminum | 0.027 |
| Tin | 0.11 |
| Tungsten | 0.055 |
| Zinc | 0.061 |
| Copper | 0.0178 |

$$R = \frac{\rho * l}{A}$$

R: resistance value of the wire [ohm]
ρ: specific resistance [Ohm*mm/m]
l: length of the wire [m]
A: cross section of the wire [mm2]

Example Calculation for Tin:

| | |
| --- | --- |
| Spec. resistance | 0.11 ohm mm2/m |
| Cross section | 0.01 mm2 |
| Length | 0.01 m |
| Resistance | R = 0.11 ohm |

Electrical Power

The energy source in the patch pump can ideally supply 0.5 W for several seconds. This has an influence on the design and configuration of the heat source. The heating element or the heat source must heat up the medium with the available electrical power and cause it to move/flow aside.

A variety of media can be considered as heat sources.

SMD Resistor

Resistors used for surface mounting in electronics are available in differently sized designs. They are very durable and the same resistor can be used during several melting processes. Owing to their design and contacting, the heat dissipation to the connecting conductors is relatively high. The advantage is that they are very temperature-resistant.

The temperature resistance is provided by the production process—the resistive paste is fired at 850° C. This makes the resistor also very robust against mechanical damage. Furthermore, such resistors are mass-produced, which makes them very inexpensive.

Customized Resistor Design

A specific design of the substrate could be produced according to the principle of the SMD resistor. The substrate is equipped with a resistor layer at the desired point. The advantage of this variant, in addition to heat resistance and robustness against mechanical damage, is particularly the lower heat capacity and the possibility of designing the geometry individually, which can markedly increase the efficiency.

Resistor Printing on Circuit Boards (Printed Polymers)

The technology of resistor printing on circuit boards is frequently used in operating elements such as buttons and rotary potentiometers in operating elements.

Carbon varnish can be used for resistors printed directly on circuit boards. To accomplish this, the gap between two circuit boards is covered by an area of carbon varnish. In this area, the circuit board is solder stop varnish. The resistance is equal to the specific surface resistance [W (per square)] multiplied by the ratio of distance to width of the carbon varnish:

Carbon pastes having a surface resistance of 10 ohms to 1000 kohm are available. Resistances from a few ohms to several tens of kohms can be generated by using different varnish geometries (e.g. meanders). The tolerance of the resistance in the final application is approximately 30% without laser calibration and 5% with laser calibration. The layer thickness of the paste is 20 μm. The minimum width of the structure such as the meander is 0.2 mm.

The advantages of this variant include the very low heat capacity, which leads to very fast heating. Furthermore, the shape of the resistor can be selected very freely and the production is very cost-effective.

Resistor Printing on a Substrate with Aerosol Jet Printing Process

Printing on almost any substrate materials and shapes with resistive pastes. A variety of resistive pastes can be selected.

The advantages are that a substrate can be selected that has a very high thermal insulation and low heat capacity. Another advantage is the possibility of designing the heating surface three-dimensionally, and thereby increasing the heat coupling with the fusible element. The technology enables the production of very small structures, which makes a very low heat capacity possible.

LIST OF REFERENCE NUMBERS

1 Cannula housing
1.1 Blocking or (retaining)/holding element or triggering element inserter
1.1a Drive face or slope (e.g., bevel)
1.2 Insertion finger (e.g., reverser guide, process control, cannula housing finger)
1.2a Narrow decoupling region
1.2b Wide coupling region
2 Soft cannula holder
2.1 Coupling or triggering element (e.g., tongue or triggering element reverser, coupling element)
2.2 Mount or guide (e.g., soft cannula mounting)
2.3 Opening for the insertion finger
2.4 Sop or contact surface for insertion spring
2.5 Contact or stop surface for hard cannula holder
3 Hard cannula holder
3.1 Mating coupling element or tongue (e.g., tongue reverser or counter-coupling element)
3.2 Hard cannula mounting (e.g., hard cannula guide)
4 Insertion spring
5 Retraction spring
6 Cannula guide (e.g., external guide)
6.1 Cannula guide (e.g., internal guide)
7 Soft cannula
8 Hard cannula (e.g., steel cannula)
8.1 Cannula element (e.g., loop or arc-shaped structure)
9 Safety (element) or fusible safety
9.1 Connecting element
9.2a, b Mounting
9.3 Softening element, melting element
9.4 Melting element (e.g. softening element)
9.5 Retaining element (e.g., holding element, plate, softening element, melting element)
9.6 Fusible medium (e.g., softening element, melting element)
10 Warming or heating element
10a, b Milled cut
10c Electric contact
11 Pump, reservoir
12 Adhesive surface (patch pump)
13 Battery
14 Guide elements (e.g., hollow cylinder)
14a, b Outflow opening
15 Tappet
16 Film
16a, b, c Application regions
17 Adhesive surface (e.g., sticking surface; retaining element)
18 Base element
19 Structure (e.g., glued structure)

What is claimed is:

1. An insertion mechanism for a cannula, comprising:
a cannula housing, relative to which the cannula is displaceable;
at least one cannula holder to which the cannula is fastenable and which is movable relative to the cannula housing;
an insertion spring for generating an insertion force onto the at least one cannula holder;
a triggering element that can retain the at least one cannula holder relative to the cannula housing against the force generated by the insertion spring; and
a safety mechanism which holds the triggering element in a blocking position in a safety state and releases the triggering element in a triggered state such that the triggering element is movable into a release position and the at least one cannula holder can move, driven by the insertion spring, relative to the cannula housing in order to carry out an insertion movement or insertion of the cannula,
wherein the safety mechanism is under a compressive stress from the triggering element and presses against a supporting element,
wherein the triggering element is releasable by heating the safety mechanism, and
wherein the compressively stressed safety mechanism is guided in at least one guide element or guide, which enables a displacement of the compressively stressed safety mechanism.

2. An insertion mechanism for a cannula, comprising:
a cannula housing, relative to which the cannula is displaceable;
at least one cannula holder to which the cannula is fastenable and which is movable relative to the cannula housing;
an insertion device for generating an insertion force onto the at least one cannula holder;
a triggering element that can retain the at least one cannula holder relative to the cannula housing against the force generated by the insertion device; and
a safety mechanism which holds the triggering element in a blocking position in a safety state and releases the triggering element in a triggered state such that the triggering element is movable into a release position and the at least one cannula holder can move, driven by the insertion force of the insertion device, relative to the cannula housing in order to carry out an insertion movement or insertion of the cannula,
wherein the safety mechanism comprises a softenable or fusible material provided on a heating element, which is heatable and softened by the heating element from a side and/or on a surface and/or weakened with respect to a mechanical carrying or holding capacity of the softenable or fusible material, or severed or at least partially or completely melted, and
wherein the safety mechanism is under a compressive stress from the triggering element and presses against the heating element.

3. The insertion mechanism according to claim 2, wherein the safety mechanism is heated only from a single side or only on a single surface.

4. The insertion mechanism according to claim 2, wherein the safety mechanism is not clasped or surrounded for heating.

5. The insertion mechanism according to claim 2, wherein the triggering element is integrally and/or form-fittingly connected to the safety mechanism.

6. The insertion mechanism according to claim 2, wherein the fusible or softenable material is coupled to the triggering element such that the fusible or softenable material is under tensile stress in the safety state, or is coupled to the triggering element such that the fusible or softenable material is under a compressive stress in the safety state.

7. The insertion mechanism according to claim 2, wherein the safety mechanism has a tapered portion which is situated in a warming or heating region of the safety mechanism.

8. The insertion mechanism according to claim 2, wherein the cannula is a soft cannula, a hard cannula, or a soft cannula surrounding a hard cannula, or a soft cannula surrounded by a hard cannula.

9. The insertion mechanism according to claim 2, wherein the insertion device comprises a compression spring that exerts a compressive force onto the at least one cannula holder, or a tensile spring that exerts a tensile force onto the at least one cannula holder.

10. The insertion mechanism according to claim 2, wherein the cannula comprises a hard cannula, and the insertion mechanism further comprises a retraction device for retracting a hard cannula.

11. The insertion mechanism according to claim 2, wherein the safety mechanism is formed of a conductive material or a conductive plastic.

12. The insertion mechanism according to claim 2, wherein the insertion mechanism is a component of an administration device for administering a substance, the administration device comprising a reservoir for the substance and/or a pump which is connected to a proximal end of the cannula.

13. The insertion mechanism according to claim 2, wherein:
the safety mechanism is configured to be released by an electrical signal or by current flow by the heating element arranged on the side of the safety mechanism, such that
when the safety mechanism is warmed up and weakened or softened or melted, the safety mechanism releases the triggering element, and
the triggering element is pushed or pulled by a force of the insertion device into the release position.

14. The insertion mechanism according to claim 13, wherein the electrical signal is a current flow through the heating element or the safety mechanism.

15. An insertion mechanism for a cannula, comprising:
a cannula housing, relative to which the cannula is displaceable;
at least one cannula holder to which the cannula is fastenable and which is movable relative to the cannula housing;
an insertion spring for generating an insertion force onto the at least one cannula holder;
a triggering element that can retain the at least one cannula holder relative to the cannula housing against the force generated by the insertion spring;
a safety mechanism which holds the triggering element in a blocking position in a safety state and releases the triggering element in a triggered state such that the triggering element is movable into a release position and the at least one cannula holder can move, driven by the insertion spring, relative to the cannula housing in order to carry out an insertion movement or insertion of the cannula, wherein the safety mechanism is under a compressive stress from the triggering element and presses against a supporting element; and
a warming or heating element that is arranged on or at the safety mechanism as the supporting element, wherein the triggering element is releasable by heating the safety mechanism.

16. The insertion mechanism according to claim 15, wherein the safety mechanism is configured to be softened or melted or weakened by warming up and/or the safety mechanism includes a material which, in a warmed-up state, can no longer withstand the pressure exerted by the triggering element and releases the triggering element.

17. The insertion mechanism according to claim 15, wherein the safety mechanism is released when the supporting element or at least a part thereof is warmed up or softened or melted such that the compressively stressed safety mechanism enables the triggering element to reach the release position.

18. The insertion mechanism according to claim 15, wherein the compressively stressed safety mechanism is an elongated element or a rod-like element.

19. The insertion mechanism according to claim 15, wherein the supporting element is constructed of solder or a soldering means.

20. The insertion mechanism according to claim 15, wherein the safety mechanism is formed of a conductive material or a conductive plastic.

21. The insertion mechanism according to claim 15, wherein the insertion spring is a component of an administration device for administering a substance, the administration device comprising a reservoir for the substance and/or a pump which is connected to a proximal end of the cannula.

22. The insertion mechanism according to claim 15, wherein:
    the safety mechanism is released by an electrical signal,
    the safety mechanism releases the triggering element, and
    the triggering element is pushed or pulled by the force of the insertion spring into the release position.

* * * * *